US008642542B2

(12) United States Patent
Ballance

(10) Patent No.: US 8,642,542 B2
(45) Date of Patent: *Feb. 4, 2014

(54) RECOMBINANT FUSION PROTEINS TO GROWTH HORMONE AND SERUM ALBUMIN

(75) Inventor: David James Ballance, Nottingham (GB)

(73) Assignee: Novozymes Biopharma DK A/S, Bagsvaerd (DK)

( * ) Notice: Subject to any disclaimer, the term of this patent is extended or adjusted under 35 U.S.C. 154(b) by 561 days.

This patent is subject to a terminal disclaimer.

(21) Appl. No.: 12/471,168

(22) Filed: May 22, 2009

(65) Prior Publication Data

US 2010/0261650 A1  Oct. 14, 2010
US 2011/0281800 A9  Nov. 17, 2011

Related U.S. Application Data

(60) Continuation of application No. 11/315,035, filed on Dec. 23, 2005, now Pat. No. 7,550,432, which is a division of application No. 09/984,010, filed on Oct. 26, 2001, now Pat. No. 7,045,318, which is a continuation of application No. 09/091,873, filed as application No. PCT/GB96/03164 on Dec. 19, 1996, now abandoned.

(30) Foreign Application Priority Data

Dec. 30, 1995  (GB) .................................. 9526733.2

(51) Int. Cl.
*A61K 38/00* (2006.01)
*C07K 14/765* (2006.01)
*C12N 1/00* (2006.01)
*C12N 1/20* (2006.01)

(52) U.S. Cl.
USPC ...... 514/5.1; 435/252.3; 435/254.2; 435/325; 435/410; 530/363; 536/23.4; 514/15.2

(58) Field of Classification Search
None
See application file for complete search history.

(56) References Cited

U.S. PATENT DOCUMENTS

| | | | |
|---|---|---|---|
| 4,595,658 A | 6/1986 | Zinder et al. | |
| 4,601,980 A | 7/1986 | Goeddel et al. | |
| 4,765,980 A | 8/1988 | DePrince et al. | |
| 4,894,332 A | 1/1990 | Schaller et al. | |
| 5,045,312 A | 9/1991 | Aston et al. | |
| 5,223,408 A | 6/1993 | Goeddel et al. | |
| 5,223,409 A | 6/1993 | Ladner et al. | |
| 5,330,971 A | 7/1994 | Wells et al. | |
| 5,374,620 A * | 12/1994 | Clark et al. .................. | 514/4.8 |
| 5,470,573 A | 11/1995 | Lubitz et al. | |
| 5,506,120 A | 4/1996 | Yamamoto et al. | |
| 5,616,474 A | 4/1997 | Bolotin et al. | |
| 5,646,012 A | 7/1997 | Fleer et al. | |
| 5,658,568 A | 8/1997 | Bagshawe | |
| 5,714,377 A | 2/1998 | Tanner et al. | |
| 5,876,969 A | 3/1999 | Fleer et al. | |
| 5,889,144 A | 3/1999 | Alila et al. | |
| 6,348,327 B1 | 2/2002 | Gorman et al. | |
| 6,686,179 B2 | 2/2004 | Fleer et al. | |
| 6,905,688 B2 | 6/2005 | Rosen et al. | |
| 6,926,898 B2 | 8/2005 | Rosen et al. | |
| 6,946,134 B1 | 9/2005 | Rosen et al. | |
| 6,994,857 B2 | 2/2006 | Rosen et al. | |
| 7,026,447 B2 | 4/2006 | Rosen et al. | |
| 7,045,318 B2 | 5/2006 | Ballance | |
| 7,056,701 B2 | 6/2006 | Fleer et al. | |
| 7,094,577 B2 * | 8/2006 | Fleer et al. .................. | 435/69.7 |
| 7,141,547 B2 | 11/2006 | Rosen et al. | |
| 7,189,690 B2 | 3/2007 | Rosen et al. | |
| 7,482,013 B2 | 1/2009 | Ballance et al. | |
| 7,550,432 B2 | 6/2009 | Ballance | |
| 2002/0048571 A1 | 4/2002 | Gyuris et al. | |
| 2003/0104578 A1 | 6/2003 | Ballance | |
| 2003/0125247 A1 | 7/2003 | Rosen et al. | |
| 2003/0143191 A1 | 7/2003 | Bell et al. | |
| 2003/0147918 A1 | 8/2003 | Maertens et al. | |
| 2003/0166865 A1 | 9/2003 | Cox | |
| 2003/0187226 A1 | 10/2003 | Goodey et al. | |
| 2003/0199043 A1 | 10/2003 | Ballance et al. | |
| 2003/0219875 A1 | 11/2003 | Rosen et al. | |

(Continued)

FOREIGN PATENT DOCUMENTS

CA  2070781  4/1992
EP  0 319 641 A1  6/1989

(Continued)

OTHER PUBLICATIONS

Anonymous, "Use of Recombinant Human Albumin in the Formulation of Proteins," *Research Disclosure*, 375:516 (1995).
Baggio, L.L., et al., A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis, *Diabetes*, vol. 53, Sep. 2004, 2492-2500.
GenBank as Accession No. CAA01217 (Jul. 6, 1995).
Chang, Hsiu-Ching, et al., "A General Method for Facilitating Heterodimeric Pairing between Two Proteins: Application to Expression of α and β T-cell Receptor Extracellular Segments," *Proc. Natl. Acad. Sci.*, vol. 91, Nov. 1994, 11408-11412.

(Continued)

*Primary Examiner* — Joanne Hama
*Assistant Examiner* — Ian Dang
(74) *Attorney, Agent, or Firm* — Woodcock Washburn LLP

(57) ABSTRACT

The invention describes albumin fusion proteins comprising growth hormone and serum albumin. The invention also describes nucleic acid molecules encoding the albumin fusion proteins of the invention, as well as vectors containing these nucleic acid molecules, host cells transformed with these vectors, and methods of making the albumin fusion proteins of the invention and using these nucleic acids, vectors, and/or host cells. Additionally, the invention describes compositions comprising the albumin fusion proteins, and methods of treating patients in need of growth hormone, comprising administering the albumin fusion proteins of the invention.

17 Claims, 13 Drawing Sheets

(56) References Cited

U.S. PATENT DOCUMENTS

| | | | |
|---|---|---|---|
| 2004/0010134 | A1 | 1/2004 | Rosen et al. |
| 2005/0054051 | A1 | 3/2005 | Rosen et al. |
| 2005/0054570 | A1 | 3/2005 | Rosen et al. |
| 2005/0100991 | A1 | 5/2005 | Rosen et al. |
| 2005/0186664 | A1 | 8/2005 | Rosen et al. |
| 2005/0244931 | A1 | 11/2005 | Rosen et al. |
| 2005/0266532 | A1 | 12/2005 | Rosen et al. |
| 2005/0266533 | A1 | 12/2005 | Ballance et al. |
| 2006/0014254 | A1 | 1/2006 | Haseltine et al. |
| 2006/0084794 | A1 | 4/2006 | Rosen et al. |
| 2007/0048282 | A1 | 3/2007 | Rosen et al. |
| 2008/0167238 | A1 | 7/2008 | Rosen et al. |

FOREIGN PATENT DOCUMENTS

| | | | |
|---|---|---|---|
| EP | 0 399 666 A1 | | 11/1990 |
| EP | 0 591 524 | | 4/1994 |
| JP | 2227079 A | | 9/1990 |
| JP | 3201987 A | | 9/1991 |
| WO | WO 90/01063 A1 | | 2/1990 |
| WO | WO 90/04788 | | 5/1990 |
| WO | WO 91/08220 A1 | | 6/1991 |
| WO | WO 93/00109 A1 | | 1/1993 |
| WO | WO 93/00437 A1 | | 1/1993 |
| WO | WO 93/15199 A1 | | 8/1993 |
| WO | WO 94/03198 A1 | | 2/1994 |
| WO | WO 95/30759 | | 11/1995 |
| WO | WO 97/24445 A1 | | 7/1997 |
| WO | WO 97/26321 A2 | | 7/1997 |
| WO | WO 98/12344 A1 | | 3/1998 |
| WO | WO 01/77137 A1 | | 10/2001 |
| WO | WO 01/79258 A1 | | 10/2001 |
| WO | WO 01/79271 A1 | | 10/2001 |
| WO | WO 01/79442 A2 | | 10/2001 |
| WO | WO 01/79443 A2 | | 10/2001 |
| WO | WO 02/097038 A2 | | 12/2002 |
| WO | WO 02/097038 A3 | | 12/2002 |
| WO | WO 03/013573 A1 | | 2/2003 |
| WO | WO 03/030821 A2 | | 4/2003 |
| WO | WO 03/059934 A2 | | 7/2003 |
| WO | WO 03/060071 A2 | | 7/2003 |
| WO | WO 2005/003296 A2 | | 1/2005 |
| WO | WO 2005/077042 A2 | | 8/2005 |
| WO | WO 2007/021494 A2 | | 2/2007 |
| WO | WO 2007/146038 A2 | | 12/2007 |

OTHER PUBLICATIONS

"Clinical Trials," *Biotechnology Law Report*, 20(4):555-570 (2001).
Cunningham, B.C. et al., "Dimerization of the Extracellular Domain of the Human Growth Hormone Receptor by a Single Hormone Molecule," *Science* 254:821-825 (1991).
Denoto, F.M. et al., "Human growth hormone DNA sequence and mRNA structure: possible alternative splicing," *Nucleic Acids Research* 9:3719-3730 (1981).
De Vos, A.M. et al., "Human Growth Hormone and Extracellular Domain of its Receptor: Crystal Structure of the Complex," *Science* 255:306-312 (1992).
Ealey, P.A. et al., "The development of an eluted stain bioassay (ESTA) for human growth hormone," *Growth Regulation*, 5(1):36-44 (1995).
"Human Growth Hormone for Injection," *The European Pharmacopeia*, Monograph 556 (1987).
Extended European Search Report for European Patent Application No. 08075724.8-1212 dated Nov. 3, 2008, (9 pages).
Extended European Search Report for European Patent Application No. 05077642.6-2401 dated Oct. 25, 2006, (7 pages).
Glue, P. et al., "Pegylated interferon-α2b: Pharmacokinetics, pharmacodynamics, safety, and preliminary efficacy data," *Clinical Pharmacology & Therapeutics*, vol. 68, No. 5, 556-567 (2000).
Haffner, D., et al., "Metabolic Clearance of Recombinant Human Growth Hormone in Health and Chronic Renal Failure," *The Journal of Clinical Investigation* 93:1163-1171 (1994).
Hiramatsu, R., et al., "The Prepro-Peptide of *Mucor* Rennin Directs the Secretion of Human Growth Hormone by *Saccharomyces cerevisiae*," *Applied and Environmental Microbiology* 56:2125-2132 (1990).
Hiramatsu, R., et al., "The Secretion Leader of *Mucor pusillus* Rennin Which Possesses an Artificial Lys-Arg Sequence Directs the Secretion of Mature Human Growth Hormone by *Saccharomyces cerevisiae*," *Applied and Environmental Microbiology* 57:2052-2056 (1991).
Hollan, "HGS targets patent-expiring drugs", *Nature Biotechnology*, vol. 18, Dec. 2000, 1238-1239.
Human Genome Sciences 2001 Annual Report, 3 pages.
International Preliminary Examination Report for International Application No. PCT/GB96/03164 dated Mar. 30, 1998, (6 pages).
International Search Report for International Application No. PCT/GB96/03164 dated Jun. 13, 1997 (5 pages).
International Search Report for International Application No. PCT/US05/04041 dated Sep. 27, 2006, (3 pages).
Katakam, M. et al., "Effect of Surfactants on the Physical Stability of Recombinant Human Growth Hormone," *Journal of Pharmaceutical Sciences*, vol. 84, No. 6, Jun. 1995, 713-716.
Kearns, G.L., et al., "Single and Multiple Dose Pharmacokinetics of Methionyl Growth Hormone in Children with Idiopathic Growth Hormone Deficiency," *Journal of Clinical Endocrinology and Metabolism* 72:1148-1156 (1991).
Kerry-Williams, S.M. et al., "Disruption of the *Saccharomyces cerevisiae* YAP3 Gene Reduces the Proteolytic Degradation of Secreted Recombinant Human Albumin," *Yeast*, vol. 14, 161-169 (1998).
Li, C.H., "Human Growth Hormone: 1974-1981," *Molecular and Cellular Biochemistry* 46:31-41 (1982).
Martial, J.A. et al., "Human Growth Hormone: Complementary DNA Cloning and Expression in Bacteria," *Science* 205:602-607 (1979).
Matsushita, S. et al., "Functional Analysis of Recombinant Human Serum Albumin Domains for Pharmaceutical Applications," *Pharmaceutical Research*, vol. 21, No. 10, Oct. 2004, 1924-1932.
Nomura, N., et al., "Secretion by *Saccharomyces cerevisiae* of Human Apolipoprotein E as a Fusion to Serum Albumin," *Biosci. Biotech. Biochem.*, 59:532-534 (1995).
Osborn, B.L. et al., "Pharmacokinetic and Pharmacodynamic Studies of a Human Serum Albumin-Interferon-α Fusion Protein in Cynomolgus Monkeys," *The Journal of Pharmacology and Experimental Therapeutics*, vol. 303, No. 2, 540-548 (2002).
Osborn, B.L. et al., "Albutropin: A growth hormone-albumin fusion with improved pharmacokinetics and pharmacodynamics in rats and monkeys," *European J. of Pharmacology* 456:149-158 (2002).
Paige, A., et al., "Prolonged Circulation of Recombinant Human Granulocyte-Colony Stimulating Factor by Covalent Linkage to Albumin Through a Heterobifunctional Polyethylene Glycol," *Pharmaceutical Research* 12:1883-1888 (1995).
Pearlman, R. et al., "Stability and Characterization of Human Growth Hormone," *Pharmaceutical Biotechnology* 5:1-58 (1993).
Pinkert, C.A., et al., "An Albumin Enhancer Located 10 kb Upstream Functions Along with its Promoter to Direct Efficient, Liver-Specific Expression in Transgenic Mice," *Genes and Development* 1:268-276 (1987).
Poznansky, M.J., et al., "Growth Hormone-Albumin Conjugates Reduced Renal Toxicity and Altered Plasma Clearance," *FEBS Letters* 239:18-22 (1988).
"Regulatory Affairs—Pharmaceutical," *Biotechnology Law Report*, 20(2):182-188 (2001).
Sleep, D., et al., "The Secretion of Human Serum Albumin from the Yeast *Saccharomyces cerevisiae* Using Five Different Leader Sequences," *Bio/Technology*, vol. 8, Jan. 1990, 42-46.
Strobl, J.S., et al., "Human Growth Hormone," *Pharmacological Reviews* 46:1-34 (1994).
Subramanian, G.M., et al., "Albinterferon α-2b: A genetic fusion protein for the treatment of chronic hepatitis C," *Nature Biotechnology*, vol. 25, No. 12, Dec. 2007, 1411-1419.
Tan, Seng-Lai, et al., "Hepatitis C. Therapeutics: Current Status and Emerging Strategies," *Nature Reviews*, vol. 1, Nov. 2002, 867-881.
Tokunaga, T., et al., "Expression of a Synthetic Human Growth Hormone Gene in Yeast," *Gene* 39:117-120 (1985).

(56) References Cited

OTHER PUBLICATIONS

Traub, A. et al., "Interferon-albumin conjugate with conserved biological activity," *J. Gen. Virol.*, 53:389-392 (1981).

Tsiomenko, A.B., et al., "Prosegment of Yeast α-Factor Directs a Heterologous Protein (Human Growth Hormone) to the Culture Medium of *Saccharomyces cerevisiae*," *Biochemistry* 59:1247-1256 (1994).

Uhlen, M., et al., "Gene Fusions for Purpose of Expression: An Introduction," *Gene Expression Technology* 185:129-143 (1990).

Yeh, P. et al., "Design of Yeast-secreted Albumin Derivatives for Human Therapy: Biological and Antiviral Properties of a Serum Albumin-CD4 Genetic Conjugate," *Proc. Natl., Acad. Sci.*, vol. 89, Mar. 1992, 1904-1908.

Zeisel, H.J., et al., "Pharmacokinetics and Short-Term Metabolic Effects of Mammalian Cell-Derived Biosynthetic Human Growth in Man," *Hormone Research* 37 (suppl 2):5-13 (1992).

Written Opinion for International Application No. PCT/GB96/03164 dated Oct. 13, 1997, (4 pages).

* cited by examiner

```
      F   P   T   I   P   L   S   R   L   F   D   N   A   M   L   R   A   H   R
     TTC CCA ACC ATT CCC TTA TCC AGG CTT TTT GAC AAC GCT ATG CTC CGC GCC CAT CGT
                                                                              ^50
      L   H   Q   L   A   F   D   T   Y   Q   E   F   E   E   A   Y   I   P   K
     CTG CAC CAG CTG GCC TTT GAC ACC TAC CAG GAG TTT GAA GAA GCC TAT ATC CCA AAG
                                                                          ^100
      E   Q   K   Y   S   F   L   Q   N   P   Q   T   S   L   C   F   S   E   S
     GAA CAG AAG TAT TCA TTC CTG CAG AAC CCC CAG ACC TCC CTC TGT TTC TCA GAG TCT
                                                          ^150
      I   P   T   P   S   N   R   E   E   T   Q   Q   K   S   N   L   E   L   L
     ATT CCG ACA CCC TCC AAC AGG GAG GAA ACA CAA CAG AAA TCC AAC CTA GAG CTG CTC
                                              ^200
      R   I   S   L   L   L   I   Q   S   W   L   E   P   V   Q   F   L   R   S
     CGC ATC TCC CTG CTG CTC ATC CAG TCG TGG CTG GAG CCC GTG CAG TTC CTC AGG AGT
                                  ^250
      V   F   A   N   S   L   V   Y   G   A   S   D   S   N   V   Y   D   L   L
     GTC TTC GCC AAC AGC CTG GTG TAC GGC GCC TCT GAC AGC AAC GTC TAT GAC CTC CTA
                              ^300
      K   D   L   E   E   G   I   Q   T   L   M   G   R   L   E   D   G   S   P
     AAG GAC CTA GAG GAA GGC ATC CAA ACG CTG ATG GGG AGG CTG GAA GAT GGC AGC CCC
                  ^350
      R   T   G   Q   I   F   K   Q   T   Y   S   K   F   D   T   N   S   H   N
     CGG ACT GGG CAG ATC TTC AAG CAG ACC TAC AGC AAG TTC GAC ACA AAC TCA CAC AAC
     ^400                                                              ^450
      D   D   A   L   L   K   N   Y   G   L   L   Y   C   F   R   K   D   M   D
     GAT GAC GCA CTA CTC AAG AAC TAC GGG CTG CTC TAC TGC TTC AGG AAG GAC ATG GAC
                                                                  ^500
      K   V   E   T   F   L   R   I   V   Q   C   R   S   V   E   G   S   C   G
     AAG GTC GAG ACA TTC CTG CGC ATC GTG CAG TGC CGC TCT GTG GAG GGC AGC TGT GGC
                                                                  ^550
      F       (SEQ ID NO: 23)
     TTC TAG  (SEQ ID NO: 22)
```

Figure 1

```
  D   A   H   K   S   E   V   A   H   R   F   K   D   L   G   E   E   N   P
GAT GCA CAC AAG AGT GAG GTT GCT CAT CGG TTT AAA GAT TTG GGA GAA GAA AAT TTC
  K   A   L   V   L   I   A   F   A   Q   Y   L   Q   Q   C   P   F   E   D
AAA GCC TTG GTG TTG ATT GCC TTT GCT CAG TAT CTT CAG CAG TGT CCA TTT GAA GAT
                                                        ^100
  H   V   K   L   V   N   E   V   T   E   F   A   K   T   C   V   A   D   E
CAT GTA AAA TTA GTG AAT GAA GTA ACT GAA TTT GCA AAA ACA TGT GTT GCT GAT GAG
  S   A   E   N   C   D   K   S   L   H   T   L   F   G   D   K   L   C   T
TCA GCT GAA AAT TGT GAC AAA TCA CTT CAT ACC CTT TTT GGA GAC AAA TTA TGC ACA
                                    ^200
  V   A   T   L   R   E   T   Y   G   E   M   A   D   C   C   A   K   Q   E
GTT GCA ACT CTT CGT GAA ACC TAT GGT GAA ATG GCT GAC TGC TGT GCA AAA CAA GAA
  P   E   R   N   E   C   F   L   Q   H   K   D   D   N   P   N   L   P   R
CCT GAG AGA AAT GAA TGC TTC TTG CAA CAC AAA GAT GAC AAC CCA AAC CTC CCC CGA
                ^300
  L   V   R   P   E   V   D   V   M   C   T   A   F   H   D   N   E   E   T
TTG GTG AGA CCA GAG GTT GAT GTG ATG TGC ACT GCT TTT CAT GAC AAT GAA GAG ACA
  F   L   K   K   Y   L   Y   E   I   A   R   R   H   P   Y   F   Y   A   P
TTT TTG AAA AAA TAC TTA TAT GAA ATT GCC AGA AGA CAT CCT TAC TTT TAT GCC CCG
^400
  E   L   L   F   F   A   K   R   Y   K   A   A   F   T   E   C   C   Q   A
GAA CTC CTT TTC TTT GCT AAA AGG TAT AAA GCT GCT TTT ACA GAA TGT TGC CAA GCT
                                                            ^500
  A   D   K   A   A   C   L   L   P   K   L   D   E   L   R   D   E   G   K
GCT GAT AAA GCT GCC TGC CTG TTG CCA AAG CTC GAT GAA CTT CGG GAT GAA GGG AAG
  A   S   S   A   K   Q   R   L   K   C   A   S   L   Q   K   F   G   E   R
GCT TCG TCT GCC AAA CAG AGA CTC AAG TGT GCC AGT CTC CAA AAA TTT GGA GAA AGA
                                ^600
  A   F   K   A   W   A   V   A   R   L   S   Q   R   F   P   K   A   E   F
GCT TTC AAA GCA TGG GCA GTA GCT CGC CTG AGC CAG AGA TTT CCC AAA GCT GAG TTT
  A   E   V   S   K   L   V   T   D   L   T   K   V   H   T   E   C   C   H
GCA GAA GTT TCC AAG TTA GTG ACA GAT CTT ACC AAA GTC CAC ACG GAA TGC TGC CAT
                        ^700
  G   D   L   L   E   C   A   D   D   R   A   D   L   A   K   Y   I   C   E
GGA GAT CTG CTT GAA TGT GCT GAT GAC AGG GCG GAC CTT GCC AAG TAT ATC TGT GAA
  N   Q   D   S   I   S   S   K   L   K   E   C   C   E   K   P   L   L   E
AAT CAA GAT TCG ATC TCC AGT AAA CTG AAG GAA TGC TGT GAA AAA CCT CTG TTG GAA
^800
  K   S   H   C   I   A   E   V   E   N   D   E   M   P   A   D   L   P   S
AAA TCC CAC TGC ATT GCC GAA GTG GAA AAT GAT GAG ATG CCT GCT GAC TTG CCT TCA
                                                        ^900
```

Figure 6A

```
L   A   A   D   F   V   E   S   K   D   V   C   K   N   Y   A   E   A   K
TTA GCT GCT GAT TTT GTT GAA AGT AAG GAT GTT TGC AAA AAC TAT GCT GAG GCA AAG
D   V   F   L   G   M   F   L   Y   E   Y   A   R   R   H   P   D   Y   S
GAT GTC TTC CTG GGC ATG TTT TTG TAT GAA TAT GCA AGA AGG CAT CCT GAT TAC TCT
                                    ^1000
V   V   L   L   L   R   L   A   K   T   Y   E   T   T   L   E   K   C   C
GTC GTG CTG CTG CTG AGA CTT GCC AAG ACA TAT GAA ACC ACT CTA GAG AAG TGC TGT
A   A   A   D   P   H   E   C   Y   A   K   V   F   D   E   F   K   P   L
GCC GCT GCA GAT CCT CAT GAA TGC TAT GCC AAA GTG TTC GAT GAA TTT AAA CCT CTT
                ^1100
V   E   E   P   Q   N   L   I   K   Q   N   C   E   L   F   E   Q   L   G
GTG GAA GAG CCT CAG AAT TTA ATC AAA CAA AAT TGT GAG CTT TTT GAG CAG CTT GGA
E   Y   K   F   Q   N   A   L   L   V   R   Y   T   K   K   V   P   Q   V
GAG TAC AAA TTC CAG AAT GCG CTA TTA GTT CGT TAC ACC AAG AAA GTA CCC CAA GTG
  ^1200
S   T   P   T   L   V   E   V   S   R   N   L   G   K   V   G   S   K   C
TCA ACT CCA ACT CTT GTA GAG GTC TCA AGA AAC CTA GGA AAA GTG GGC AGC AAA TGT
                                                                        ^1300
C   K   H   P   E   A   K   R   M   P   C   A   E   D   Y   L   S   V   V
TGT AAA CAT CCT GAA GCA AAA AGA ATG CCC TGT GCA GAA GAC TAT CTA TCC GTG GTC
L   N   Q   L   C   V   L   H   E   K   T   P   V   S   D   R   V   T   K
CTG AAC CAG TTA TGT GTG TTG CAT GAG AAA ACG CCA GTA AGT GAC AGA GTC ACC AAA
                                            ^1400
C   C   T   E   S   L   V   N   R   P   C   F   S   A   L   E   V   D
TGC TGC ACA GAA TCC TTG GTG AAC AGG CGA CCA TGC TTT TCA GCT CTG GAA GTC GAT
E   T   Y   V   P   K   E   F   N   A   E   T   F   T   F   H   A   D   I
GAA ACA TAC GTT CCC AAA GAG TTT AAT GCT GAA ACA TTC ACC TTC CAT GCA GAT ATA
                        ^1500
C   T   L   S   E   K   E   R   Q   I   K   K   Q   T   A   L   V   E   L
TGC ACA CTT TCT GAG AAG GAG AGA CAA ATC AAG AAA CAA ACT GCA CTT GTT GAG CTC
V   K   H   K   P   K   A   T   K   E   Q   L   K   A   V   M   D   D   F
GTG AAA CAC AAG CCC AAG GCA ACA AAA GAG CAA CTG AAA GCT GTT ATG GAT GAT TTC
    ^1600
A   A   F   V   E   K   C   C   K   A   D   D   K   E   T   C   F   A   E
GCA GCT TTT GTA GAG AAG TGC TGC AAG GCT GAC GAT AAG GAG ACC TGC TTT GCC GAG
                                                                    ^1700
E   G   K   K   L   V   A   A   S   Q   A   A   L   G   L       (SEQ ID NO: 26)
GAG GGT AAA AAA CTT GTT GCT GCA AGT CAA GCT GCC TTA GGC TTA TAA (SEQ ID NO: 25)
```

RECOMBINANT FUSION PROTEINS TO GROWTH HORMONE AND SERUM ALBUMIN

This is a continuation of U.S. patent application Ser. No. 11/315,035, filed Dec. 23, 2005, now U.S. Pat. No. 7,550,432, which is a divisional of U.S. patent application Ser. No. 09/984,010, filed Oct. 26, 2001, now U.S. Pat. No. 7,045,318, which is a continuation of U.S. patent application Ser. No. 09/091,873, now abandoned, which is the National Stage of International Application No. PCT/GB96/03164, filed Dec. 19, 1996, all of which are incorporated herein by reference.

FIELD OF THE INVENTION

The present invention relates to recombinant fusion proteins, to growth hormone (GH), to serum albumin and to production of proteins in yeast.

BACKGROUND AND PRIOR ART

Human serum albumin (HSA or HA), a protein of 585 amino acids (SEQ ID NO: 26), is responsible for a significant proportion of the osmotic pressure of serum and also functions as a carrier of endogenous and exogenous ligands. At present, HSA for clinical use is produced by extraction from human blood. The production of recombinant HA (rHA) in microorganisms has been disclosed in EP 330 451 and EP 361 991.

The role of albumin as a carrier molecule and its inert nature are desirable properties for use as a stabiliser and transporter of polypeptides. The use of albumin as a component of a fusion protein for stabilising other proteins has been disclosed in WO 93/15199, WO 93/15200, and EP 413 622. The use of N-terminal fragments of HSA for fusions to polypeptides has also been disclosed (EP 399 666). Fusion to the said polypeptide is achieved by genetic manipulation, such that the DNA coding for HSA, or a fragment thereof, is joined to the DNA coding for the said polypeptide. A suitable host is then transformed or transfected with the fused nucleotide sequences, so arranged on a suitable plasmid as to express a fusion polypeptide. Nomura et al (1995) attempted to express human apolipoprotein E in *S. cerevisiae* as a fusion protein with HSA or fragments of HSA, using the HSA presequence to direct secretion. Whilst fusion to full length HSA resulted in the secretion of low levels of the protein into the medium (maximum yield of 6.3 mg per litre), fusion to HSA (1-198) or HSA (1-390) did not result in secretion into the medium.

Human growth hormone (reviewed by Strobl and Thomas, 1994) consists of a single polypeptide of 191 amino acids, internally cross-linked by two disulphide bonds. Two molecules of hGH receptor bind each molecule of hGH to facilitate signal transduction (Cunningham et al, 1991; de Vos et al, 1992). The C-terminus of the hGH molecule is involved in binding to the first receptor molecule, but the extent to which the N-terminus is involved in receptor binding is not known. The hormone is secreted from the anterior pituitary gland under hypothalamic control, and is responsible for a wide range of growth-promoting effects in the body. Clinically, hGH is used in the treatment of hypopituitary dwarfism, chronic renal insufficiency in childhood, bone fractures and burns. Current methods of production of hGH for therapeutic use are by extraction from human pituitary gland, recombinant expression in *Escherichia coli* as disclosed in EP 127 305 (Genentech) or recombinant expression in mammalian cell culture (Zeisel et al, 1992).

In addition, hGH has been expressed intracellularly in yeast (Tokunaga et al, 1985) and this organism may provide an alternative means of production as disclosed in EP 60 057 (Genentech). Tsiomenko et al (1994) reported the role of the yeast MFα-1 prepro leader sequence in the secretion of hGH from yeast. Attachment of the pre-portion of the leader sequence to the hGH gene resulted in hGH accumulation in the periplasm and vacuoles, whilst attachment of the pro-portion to hGH resulted in expression of a non-glycosylated precursor localised inside the cell. Only when both portions of the leader sequence were attached to the hGH gene was hGH secreted into the culture medium. Other secretion signals (pre-sequences) were also ineffective unless a yeast-derived pro sequence was used, suggesting that such a pro sequence was used is critical to the efficient secretion of hGH in yeast.

In humans, hGH is secreted into the blood in pulses, and in the circulation has a half-life of less than 20 minutes (Haffner et al, 1994). Elimination of the hormone is primarily via metabolism in the liver and kidneys and is more rapid in adults than in children (Kearns et al, 1991). Treatment for hGH deficiency generally lasts for 6 to 24 months, during which hGH is administered either three times a week intramuscularly or on a daily basis subcutaneously. Such a regimen of frequent administration is necessary because of the short half-life of the molecule.

Poznansky et al (1988) increased the half-life of porcine growth hormone by conjugation with either porcine or human serum albumin (HSA) to form relatively large conjugates of about 180 kD. Chemical reaction using the cross-linking reagent glutaraldehyde resulted in, on average, two molecules of albumin complexed with six molecules of growth hormone. The resulting 180 kD conjugate was found to have an extended half-life in the circulation of rats of 2 to 3 hours, compared to 5 minutes for unconjugated growth hormone. Activity assays showed that the conjugate retained full, and possibly increased activity in vitro, but was inactive in vivo.

SUMMARY OF THE INVENTION

The invention relates to proteins formed by the fusion of a molecule of albumin, or variants or fragments thereof, to a molecule of growth hormone or variants or fragments thereof, the fusion proteins having an increased circulatory half-life over unfused growth hormone. For convenience, we shall refer to human albumin (HA) and human growth hormone (hGH), but the albumin and growth hormones of other vertebrates are included also. Preferably, the fusion protein comprises HA, or a variant or fragment thereof, as the N-terminal portion, with hGH or a variant or fragment thereof as the C-terminal portion, so as to minimise any possible negative effects on receptor binding. Alternatively, a fusion protein comprising HA, or a variant or fragment thereof, as the C-terminal portion, with hGH or a variant or fragment thereof as the N-terminal portion, may also be capable of signal transduction. Generally, the polypeptide has only one HA-derived region and one GH-derived region.

Additionally, the fusion proteins of the invention may include a linker peptide between the two fused portions to provide a greater physical separation between the two moieties and thus maximise the availability of the hGH portion to bind the hGH receptor. The linker peptide may consist of amino acids such that it is flexible or more rigid.

The linker sequence may be cleavable by a protease or chemically to yield the growth hormone related moiety. Preferably, the protease is one which is produced naturally by the host, for example the *S. cerevisiae* protease kex2 or equivalent proteases. Hence, a further aspect of the invention provides a process for preparing growth hormone or a variant or fragment thereof by expressing a polynucleotide which encodes a polypeptide of the invention in a suitable host, cleaving the cleavable linker to yield the GH-type compound and recovering the GH-type compound from the host culture in a more pure form.

We have discovered that the polypeptides of the invention are significantly more stable in solution than hGH. The latter rapidly becomes inactive when stored in solution at 4° C. for over one month. Currently marketed hGH is sold as a freeze-dried powder.

Suitably, the fusion polypeptides are produced as recombinant molecules by secretion from yeast, a microorganism such as a bacterium, human cell line or a yeast. Preferably, the polypeptide is secreted from the host. We have found that, by fusing the hGH coding sequence to the HA coding sequence, either to the 5' end or 3' end, it is possible to secrete the fusion protein from yeast without the requirement for a yeast-derived pro sequence. This was surprising, as other workers have found that a yeast derived pro sequence was needed for efficient secretion of hGH in yeast. For example, Hiramitsu et al (1990, 1991) found that the N-terminal portion of the pro sequence in the *Mucor pusillus* rennin pre-pro leader was important. Other authors, using the MFα-1 signal, have always included the MFα-1 pro sequence when secreting hGH. The pro sequences were believed to assist in the folding of the hGH by acting as an intramolecular chaperone. The present invention shows that HA or fragments of HA can perform a similar function.

Hence, a particular embodiment of the invention comprises a DNA construct encoding a signal sequence effective for directing secretion in yeast, particularly a yeast-derived signal sequence (especially one which is homologous to the yeast host), and the fused molecule of the first aspect of the invention, there being no yeast-derived pro sequence between the signal and the mature polypeptide.

The *Saccharomyces cerevisiae* invertase signal is a preferred example of a yeast-derived signal.

Conjugates of the kind prepared by Poznansky et al (1988), in which separately-prepared polypeptides are joined by chemical cross-linking, are not contemplated.

The albumin or hGH may be a variant of normal HSA/rHA (termed hereinafter "HA") or hGH, respectively. By "variants" we include insertions, deletions and substitutions, either conservative or non-conservative, where such changes do not substantially alter one or more of the oncotic, useful ligand-binding and non-immunogenic properties of albumin or, in the case of hGH, its non-immunogenicity and ability to bind and activate the hGH receptor. In particular, we include naturally-occurring polymorphic variants of human albumin and fragments of human albumin, for example those fragments disclosed in EP 322 094 (namely HA (1-n), where n is 369 to 419). The albumin or growth hormone may be from any vertebrate, especially any mammal, for example human, cow, sheep, pig, hen or salmon. The albumin and GH parts of the fusion may be from differing animals.

By "conservative substitutions" is intended swaps within groups such as Gly, Ala; Val, Ile, Leu; Asp, Glu; Asn, Gln; Ser, Thr; Lys, Arg; and Phe, Tyr. The variant will usually have at least 75% (preferably at least 80%, 90%, 95% or 99%) sequence identity with a length of normal HA or hGH which is the same length as the variant and which is more identical thereto than any other length of normal HA or hGH, once the allowance is made for deletions and insertions as is customary in this art. Generally speaking, an HA variant will be at least 100 amino acids long, preferably at least 150 amino acids long. The HA variant may consist of or comprise at least one whole domain of HA, for example domains 1 (1-194), 2 (195-387), 3 (388-585), 1+2 (1-387), 2+3 (195-585) or 1+3 (1-194,+388-585). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511. Preferably, the HA part of the fusion comprises at least one subdomain or domain of HA or conservative modifications thereof. If the fusion is based on subdomains, some or all of the adjacent linker is preferably used to link to the hGH moiety. The hGH variant should have GH activity, and will generally have at least 10 amino acids, (although some authors have found activity with only 4 residues), preferably at least 20, preferably at least 50, 100, 150, 180 or 191, amino acids long, and preferably retains its cysteines for both internal disulphide bonds.

The fused molecules of the invention generally have a molecular weight of less than 100 kD, for example less than 90 kD or 70 kD. They are therefore much smaller than the 180 kD conjugates of Poznansky et al (referred to above), which were inactive in vivo. They will normally have a molecular weight of at least 20 kD, usually at least 30 kD or 50 kD. Most fall within the molecular weight range 60-90 kD.

A second main aspect of the invention provides a yeast transformed to express a fusion protein of the invention.

In addition to the transformed host cells themselves, the present invention also contemplates a culture of those cells, preferably a monoclonal (clonally homogeneous) culture, or a culture derived from a monoclonal culture, in a nutrient medium. Especially if the polypeptide is secreted, the medium will thus contain the polypeptide, with the cells, or without the cells if they have been filtered or centrifuged away.

Many expression systems are known, including bacteria (for example *E. coli* and *Bacillus subtilis*), yeasts (for example *Saccharomyces cerevisiae*, *Kluyveromyces lactis* and *Pichia pastoris*, filamentous fungi (for example *Aspergillus*), plant cells, animal cells and insect cells.

The desired protein is produced in conventional ways, for example from a coding sequence inserted in the host chromosome or on a free plasmid.

The yeasts are transformed with a coding sequence for the desired protein in any of the usual ways, for example electroporation. Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct can be grown to produce the desired polypeptide. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies.

Useful yeast plasmid vectors include pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA in accordance with the invention, if, for example, HA variants are to be prepared, is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Exemplary genera of yeast contemplated to be useful in the practice of the present invention as hosts for expressing the fusion proteins are *Pichia (Hansenula)*, *Saccharomyces*, *Kluyveromyces*, *Candida*, *Torulopsis*, *Torulaspora*, *Schizosaccharomyces*, *Citeromyces*, *Pachysolen*, *Debaromyces*, *Metschunikowia*, *Rhodosporidium*, *Leucosporidium*, *Botryoascus*, *Sporidiobolus*, *Endomycopsis*, and the like. Preferred genera are those selected from the group consisting of *Saccharomyces*, *Schizosaccharomyces*, *Kluyveromyces*, *Pichia* and *Torulaspora*. Examples of *Saccharomyces* spp. are *S. cerevisiae*, *S. italicus* and *S. rouxii*. Examples of *Kluyveromyces* spp. are *K. fragilis*, *K. lactis* and *K. marxianus*. A suitable *Torulaspora* species is *T. delbrueckii*. Examples of *Pichia (Hansenula)* spp. are *P. angusta* (formerly *H. polymorpha*), *P. anomala* (formerly *H. anomala*) and *P. pastoris*.

Methods for the transformation of *S. cerevisiae* are taught generally in EP 251 744, EP 258 067 and WO 90/01063, all of which are incorporated herein by reference.

Suitable promoters for *S. cerevisiae* include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the GUT2 promoter, the GPD1 promoter, and hybrid promoters involving hybrids of parts of 5' regulatory regions with parts of 5' regulatory regions of other promoters or with upstream activation sites (eg the promoter of EP-A-258 067).

Convenient regulatable promoters for use in *Schizosaccharomyces pombe* are the thiamine-repressible promoter from the nmt gene as described by Maundrell (1990) *J. Biol. Chem.* 265, 10857-10864 and the glucose-repressible fbp1 gene promoter as described by Hoffman & Winston (1990) *Genetics* 124, 807-816.

Methods of transforming *Pichia* for expression of foreign genes are taught in, for example, Cregg et al (1993), and various Phillips patents (eg U.S. Pat. No. 4,857,467, incorporated herein by reference), and *Pichia* expression kits are commercially available from Invitrogen BV, Leek, Netherlands, and Invitrogen Corp., San Diego, Calif. Suitable promoters include AOX1 and AOX2.

Gleeson et al (1986) *J. Gen. Microbiol.* 132, 3459-3465 include information on *Hansenula* vectors and transformation, suitable promoters being MOX1 and FMD1; whilst EP 361 991, Fleer et al (1991) and other publications from Rhône-Poulenc Rorer teach how to express foreign proteins in *Kluyveromyces* spp., a suitable promoter being PGK1.

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, ie may correspond to the promoter. Alternatively, they may be different in which case the termination signal of the *S. cerevisiae* ADH1 gene is preferred.

The desired fusion protein may be initially expressed with a secretion leader sequence, which may be any leader effective in the yeast chosen. Leaders useful in *S. cerevisiae* include that from the mating factor α polypeptide (MFα-1) and the hybrid leaders of EP-A-387 319. Such leaders (or signals) are cleaved by the yeast before the mature albumin is released into the surrounding medium. Further such leaders include those of *S. cerevisiae* invertase (SUC2) disclosed in JP 62-096086 (granted as 91/036516), acid phosphatase (PHO5), the pre-sequence of MFα-1, β-glucanase (BGL2) and killer toxin; *S. diastaticus* glucoamylase II; *S. carlsbergensis* α-galactosidase (MEL1); *K. lactic* killer toxin; and *Candida* glucoamylase.

The fusion protein of the invention or a formulation thereof may be administered by any conventional method including parenteral (eg subcutaneous or intramuscular) injection or intravenous infusion. The treatment may consist of a single dose or a plurality of doses over a period of time.

Whilst it is possible for a fusion protein of the invention to be administered alone, it is preferable to present it as a pharmaceutical formulation, together with one or more acceptable carriers. The carrier(s) must be "acceptable" in the sense of being compatible with the fusion protein and not deleterious to the recipients thereof. Typically, the carriers will be water or saline which will be sterile and pyrogen free. The formulation should be non-immunogenic; vaccine-type formulations involving adjuvants are not contemplated.

The formulations may conveniently be presented in unit dosage form and may be prepared by any of the methods well known in the art of pharmacy. Such methods include the step of bringing into association the fusion protein with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders.

Preferred unit dosage formulations are those containing a daily dose or unit, daily sub-dose or an appropriate fraction thereof, of an active ingredient.

The fusion proteins of the invention may be used in the treatment of any condition in which growth hormone is indicated, for example isolated growth hormone deficiency, panhypopituitarism, following cranial irradiation (eg in the treatment of leukaemia or brain tumours), Turner's syndrome, Down's syndrome, intrauterine growth retardation, idiopathic growth deficiency, chronic renal failure, achondroplasia, female infertility and various catabolic disorders. They may also be used in the stimulation of growth, and/or enhancement of lean meat proportion, in farm animals such as cows, sheep, goats and pigs.

The fusion protein may be administered together with insulin-like growth factor I (IGF-I).

The dosage can be calculated on the basis of the potency of the fusion protein relative to the potency of hGH, whilst taking into account the prolonged serum half-life of the fusion proteins compared to that of native hGH. Growth hormone is typically administered at 0.3 to 30.0 IU/kg/week, for example 0.9 to 12.0 IU/kg/week, given in three or seven divided doses for a year or more. In a fusion protein consisting of full length HA fused to full length GH, an equivalent dose in terms of units would represent a greater weight of agent but the dosage frequency can be reduced, for example to twice a week, once a week or less.

Preferred examples of the invention will now be described by way of example and with reference to the accompanying figures, in which:

FIG. 1 shows the human growth hormone cDNA sequence (SEQ ID NO: 22), encoding mature hGH (SEQ ID NO: 23);

Figure 7:
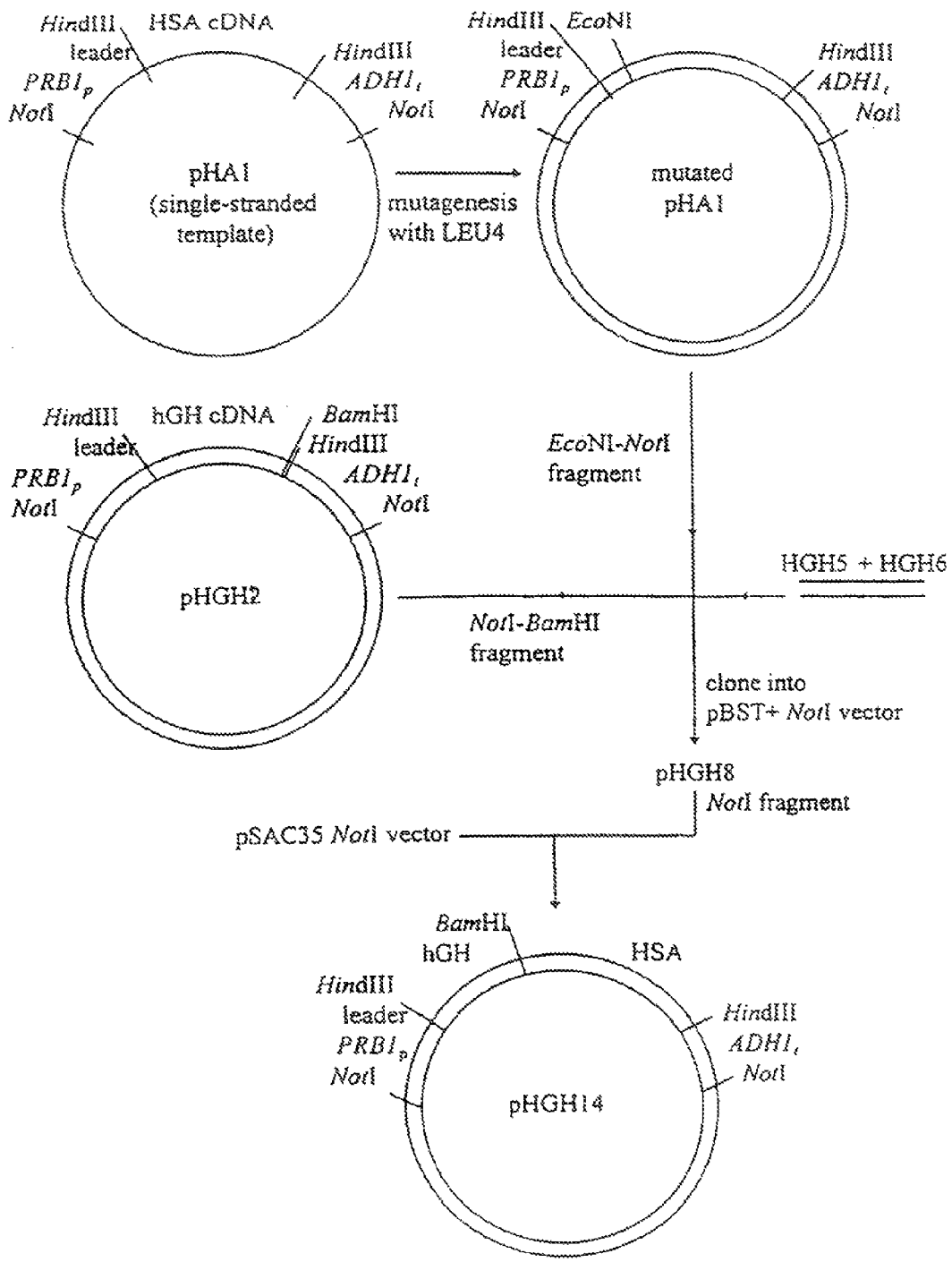
Figure 8:
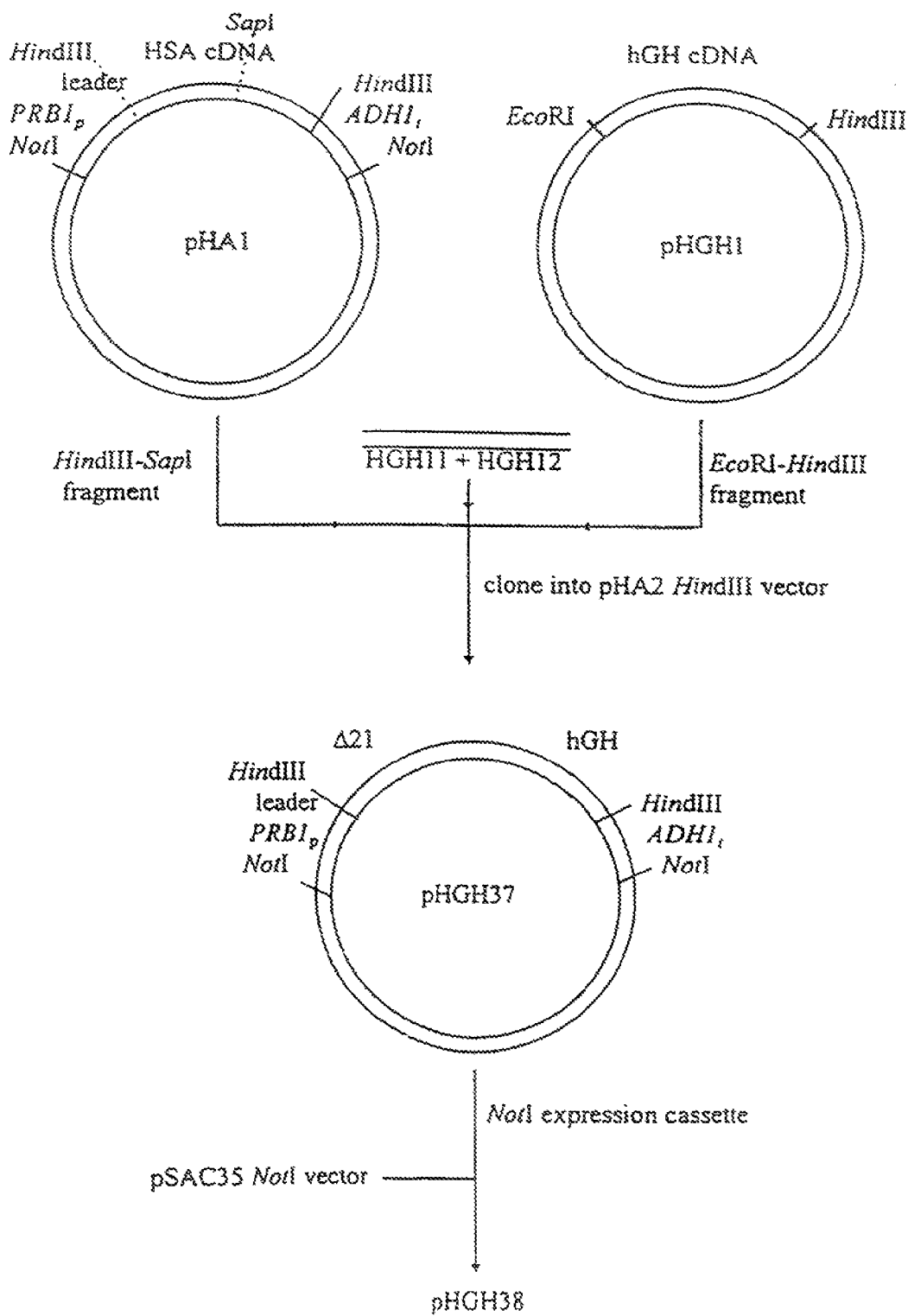
Figure 9:
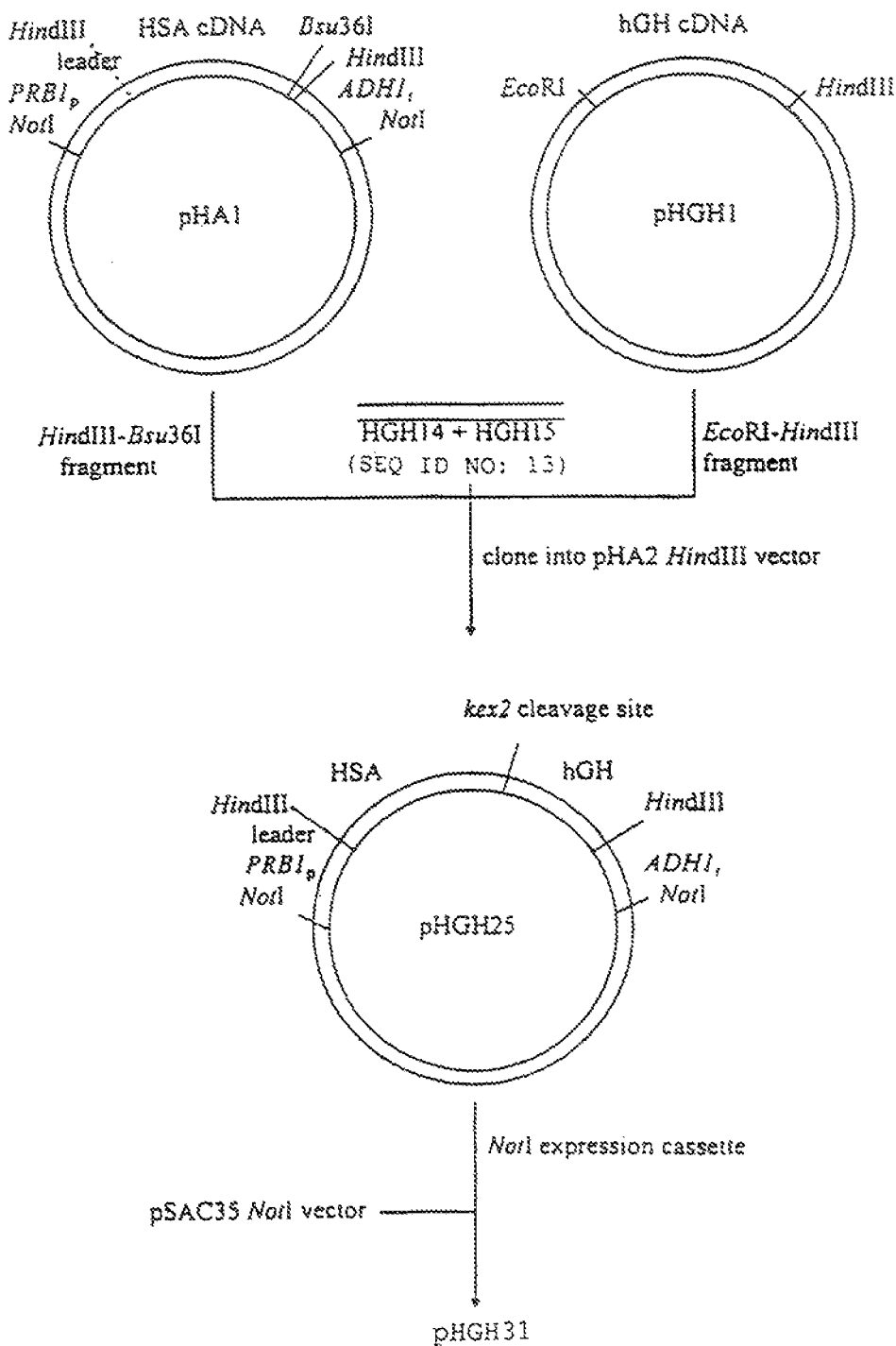
Figure 10:
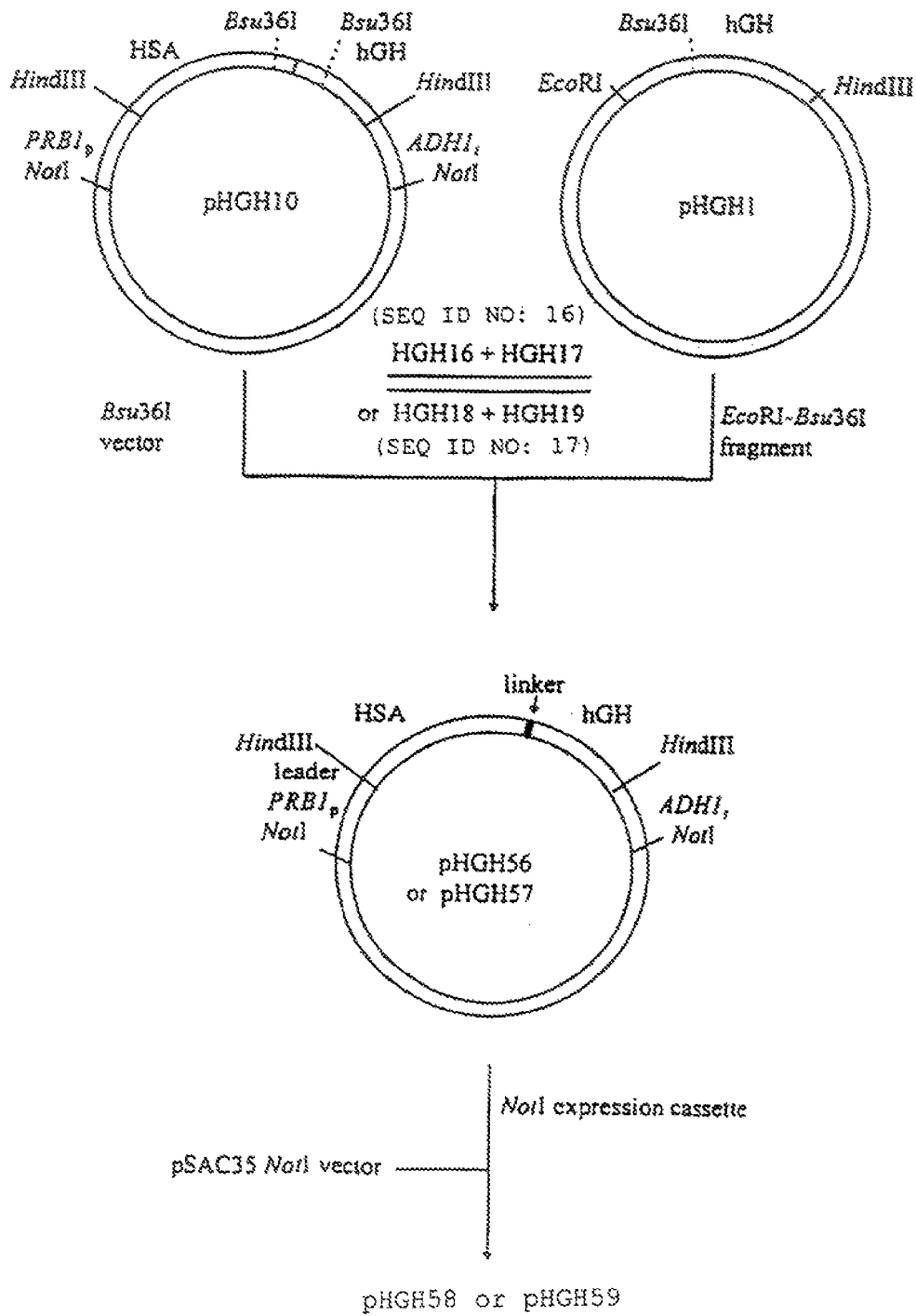
Figure 11:
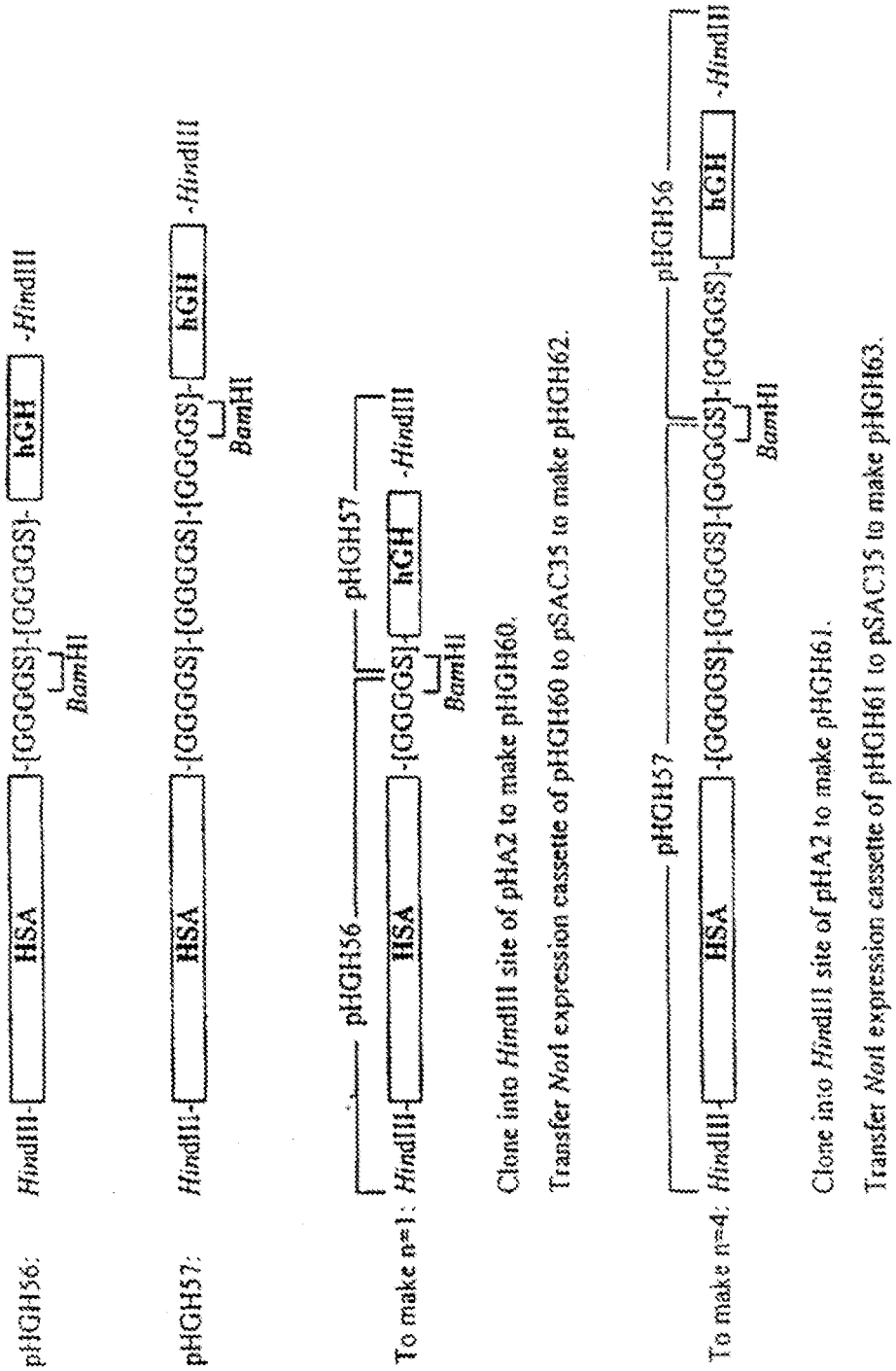

FIG. 6A-B show the HSA cDNA sequence (SEQ ID NO: 25), more particularly the region encoding the mature protein (SEQ ID NO: 26);

FIG. 7 shows the construction of pHGH14;

FIG. 8 shows the construction of pHGH38;

FIG. 9 shows the construction of pHGH31;

FIG. 10 shows the construction of pHGH58 or pHGH59 (Example 7);

FIG. 11 is a scheme for constructing fusions having spacers (Example 7); and

Figure 12:
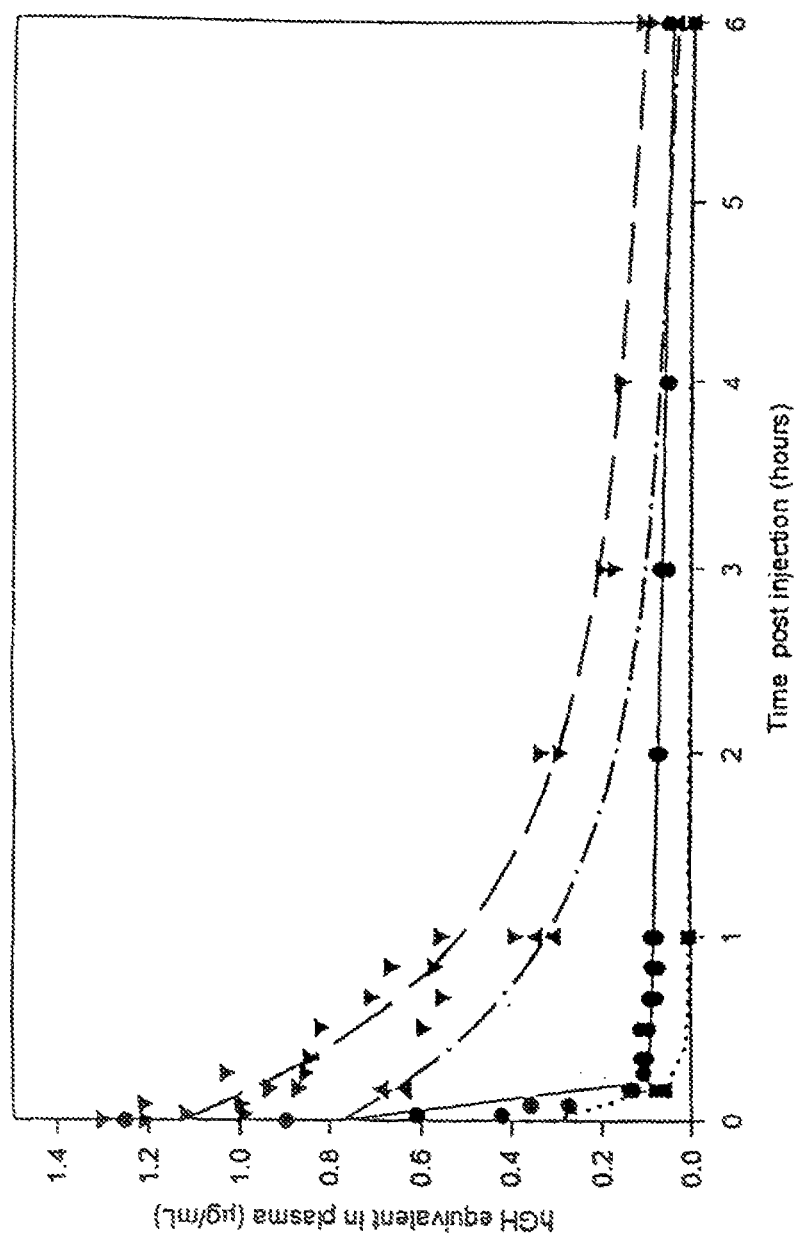

FIG. 12 shows the results of a pharmacokinetic study showing the clearance of $^{125}$I-labelled rHA-hGH compared to that of hGH following iv injection in rats. Data are from two rats in each group, and include total radioactivity and radioactivity which could be precipitated by TCA, ie that associated with protein rather than as free $^{125}$I. The calculated clearance half-life for hGH was approximately 6 minutes, compared to approximately 60 minutes for the rHA-hGH fusion protein. See Example 3.

● —hGH (total counts)
■ —hGH (TCA precipitated counts)
▼ —rHA-hGH (total counts)
▲ —rHA-hGH (TCA precipitated counts).

DETAILED DESCRIPTION OF THE INVENTION

All standard recombinant DNA procedures are as described in Sambrook et al (1989) unless otherwise stated. The DNA sequences encoding HSA were derived from the cDNA disclosed in EP 201 239.

EXAMPLE 1

Cloning of the hGH cDNA

The hGH cDNA was obtained from a human pituitary gland cDNA library (catalogue number HL1097v, Clontech Laboratories, Inc) by PCR amplification. Two oligonucleotides suitable for PCR amplification of the hGH cDNA, HGH1 and HGH2, were synthesised using an Applied Biosystems 380B Oligonucleotide Synthesiser:

```
                                          (SEQ ID NO: 1)
HGH1:   5'-CCCAAGAATTCCCTTATCCAGGC-3'

(SEQ ID NO: 2)
HGH2:   5'-GGGAAGCTTAGAAGCCACAGGATCCCTCCACAG-3'
```

HGH1 and HGH2 differed from the equivalent portion of the hGH cDNA sequence (FIG. 1, Martial et al, 1979) by two and three nucleotides, respectively, such that after PCR amplification an EcoRI site would be introduced to the 5' end of the cDNA and a BamHI site would be introduced into the 3' end of the cDNA. In addition, HGH2 contained a HindIII site immediately downstream of the hGH sequence.

PCR amplification using a Perkin-Elmer-Cetus Thermal Cycler 9600 and a Perkin-Elmer-Cetus PCR kit, was performed using single-stranded DNA template isolated from the phage particles of the cDNA library as follows: 10 μL phage particles were lysed by the addition of 10 μL phage lysis buffer (280 μg/mL proteinase K in TE buffer) and incubation at 55° C. for 15 min followed by 85° C. for 15 min. After a 1 min incubation on ice, phage debris was pelleted by centrifugation at 14,000 rpm for 3 min. The PCR mixture contained 6 μL of this DNA template, 0.1 μM of each primer and 200 μM of each deoxyribonucleotide. PCR was carried out for 30 cycles, denaturing at 94° C. for 30 s, annealing at 65° C. for 30 s and extending at 72° C. for 30 s, increasing the extension time by 1 s per cycle. Analysis of the reaction by gel electrophoresis showed a single product of the expected size (589 base pairs).

Figure 2:
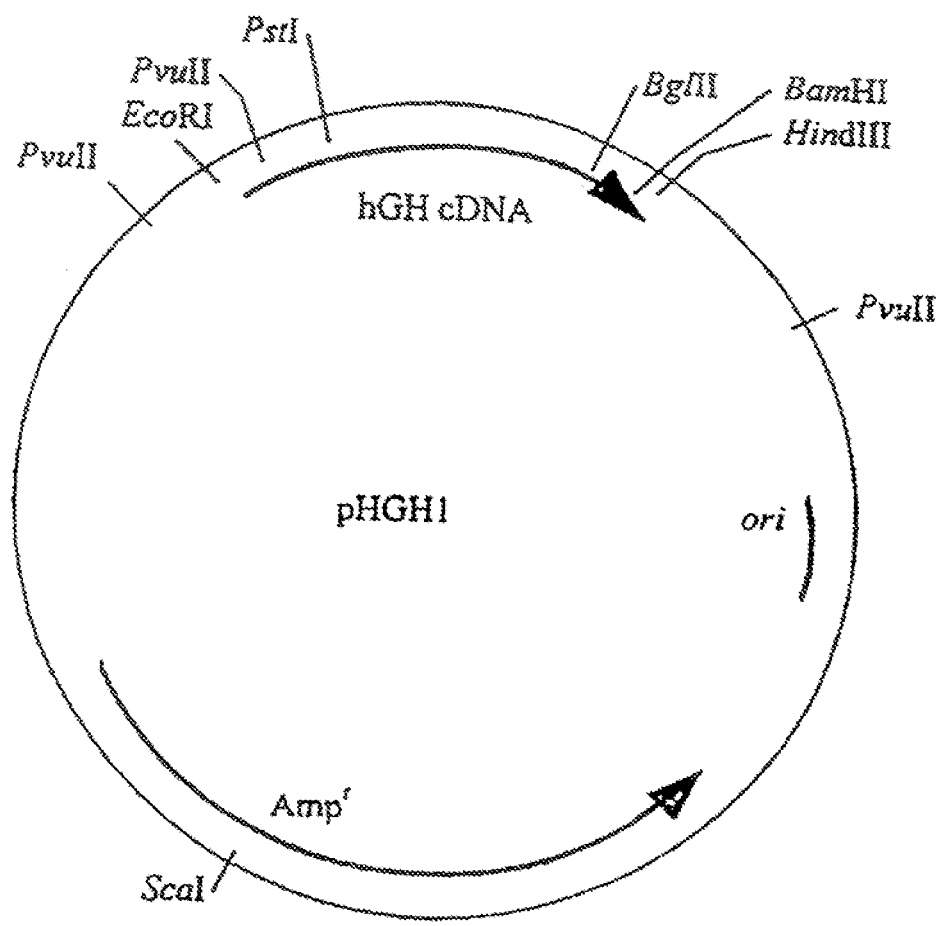
FIG. 2 shows a restriction enzyme map of pHGH1.

The PCR product was purified using Wizard PCR Preps DNA Purification System (Promega Corp) and then digested with EcoRI and HindIII. After further purification of the EcoRI-HindIII fragment by gel electrophoresis, the product was cloned into pUC19 (GIBCO BRL) digested with EcoRI and HindIII, to give pHGH1 (FIG. 2). DNA sequencing of the EcoRI-HindIII region showed that the PCR product was identical in sequence to the hGH sequence (Martial et al, 1979), except at the 5' and 3' ends, where the EcoRI and BamHI sites had been introduced, respectively.

EXAMPLE 2

Expression of the hGH cDNA

Figure 3:
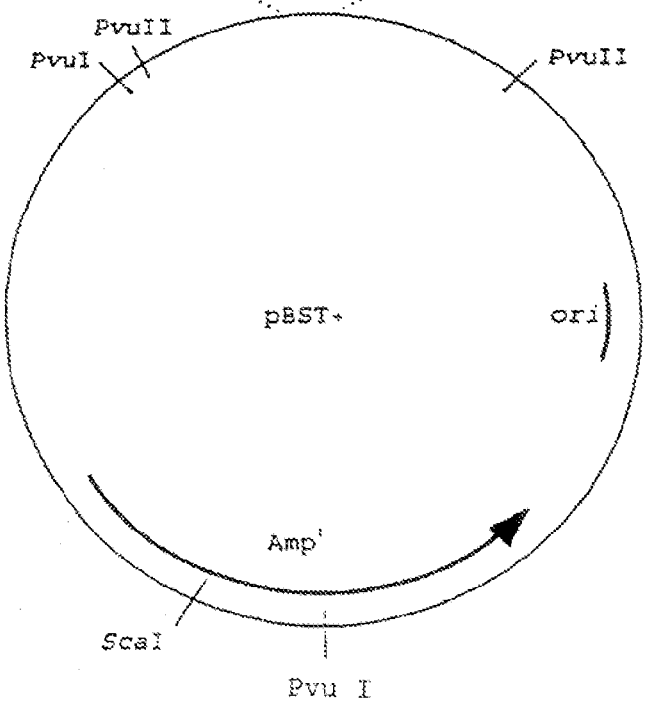
FIG. 3 shows a restriction enzyme map of pBST(+) and the DNA sequence of the polylinker (SEQ ID NO: 24)

The polylinker sequence of the phagemid pBluescribe (+) (Stratagene) was replaced by inserting an oligonucleotide linker, formed by annealing two 75-mer oligonucleotides, between the EcoRI and HindIII sites to form pBST(+) (FIG. 3). The new polylinker included a unique NotI site (the full sequence in the region of the polylinker is given in FIG. 3).

Figure 4:
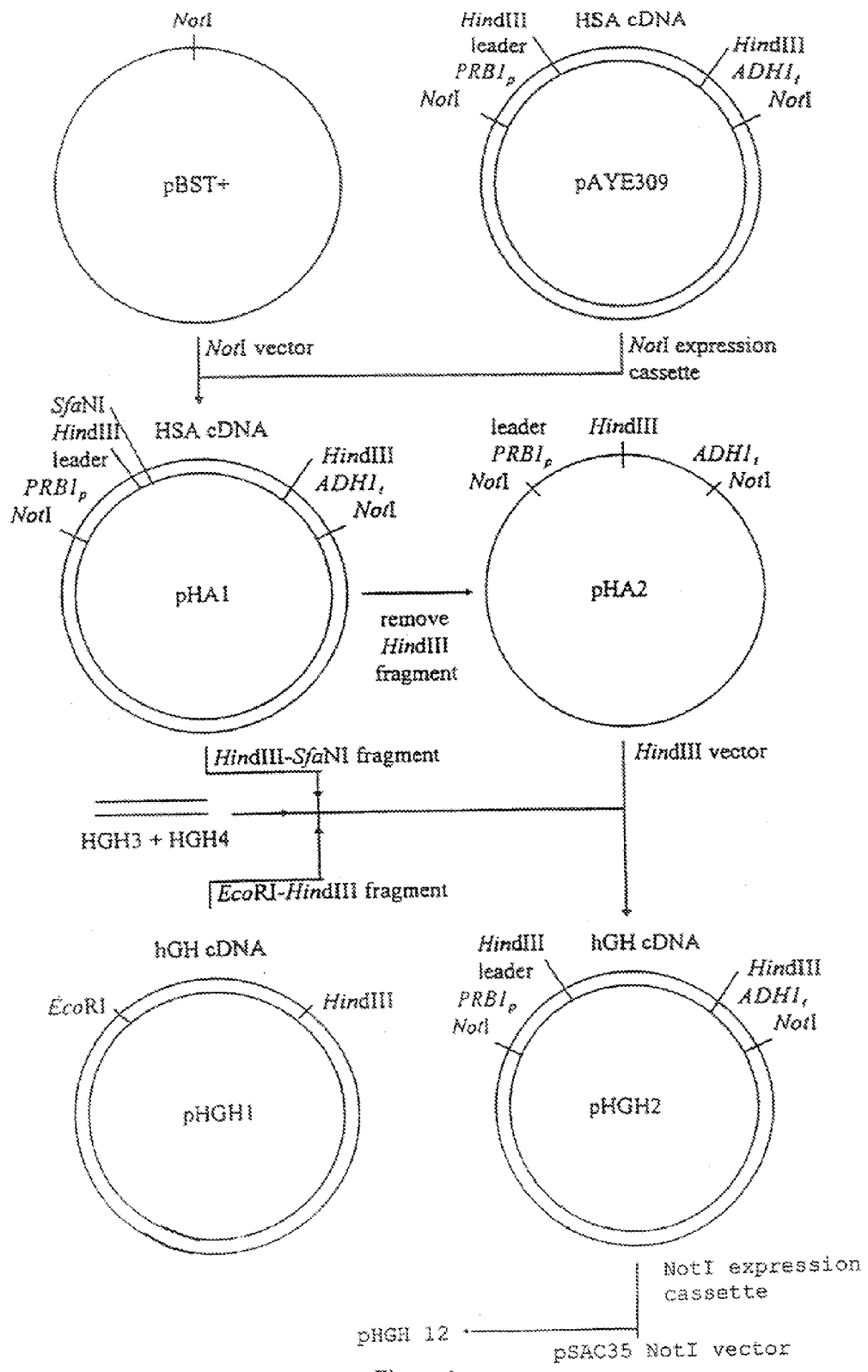
FIG. 4 shows the construction of pHGH12.

The NotI HSA expression cassette of pAYE309 (EP 431 880) comprising the PRB1 promoter, DNA encoding the HSA/MFα-1 hybrid leader sequence, DNA encoding HSA and the ADH1 terminator, was transferred to pBST(+) to form pHA1 (FIG. 4). The HSA coding sequence was removed from this plasmid by digestion with HindIII followed by religation to form pHA2 (FIG. 4).

Cloning of the hGH cDNA, as described in Example 1, provided the hGH coding region lacking the pro-hGH sequence and the first 8 base pairs (bp) of the mature hGH sequence. In order to construct an expression plasmid for secretion of hGH from yeast, a yeast promoter, signal peptide and the first 8 bp of the hGH sequence were attached to the 5' end of the cloned hGH sequence as follows:

The HindIII-SfaNI fragment from pHA1 was attached to the 5' end of the EcoRI-HindIII fragment from pHGH1 via two synthetic oligonucleotides, HGH3 and HGH4:

```
                                    (SEQ ID NO: 3)
HGH3:      5'-GATAAAGATTCCCAAC-3'

(SEQ ID NO: 4)
HGH4:      5'-AATTGTTGGGAATCTTT-3'
```

The HindIII fragment so formed was cloned into HindIII-digested pHA2 to make pHGH2 (FIG. 4), such that the hGH cDNA was positioned downstream of the PRB1 promoter and HSA/MFα-1 fusion leader sequence (WO 90/01063). The NotI expression cassette contained in pHGH2, which included the ADH1 terminator downstream of the hGH cDNA, was cloned into NotI-digested pSAC35 (Sleep et al, 1990) to make pHGH12 (FIG. 4). This plasmid comprised the entire 2 µm plasmid to provide replication functions and the LEU2 gene for selection of transformants.

pHGH12 was introduced into S. cerevisiae DB1 (Sleep et al, 1990) by transformation and individual transformants were grown for 3 days at 30° C. in 10 mL YEPD (1% w/v yeast extract, 2% w/v peptone, 2% w/v dextrose). After centrifugation of the cells, the supernatants were examined by SDS-polyacrylamide gel electrophoresis (SDS-PAGE) and were found to contain protein which was of the expected size and which was recognised by anti-hGH antiserum (Sigma, Poole, UK) on Western blots.

EXAMPLE 3

Cloning and Expression of an HSA-hGH Fusion Protein

In order to fuse the HSA cDNA to the 5' end of the hGH cDNA, the pHA1 HindIII-Bsu361 fragment (containing most of the HSA cDNA) was joined to the pHGH1 EcoRI-HindIII fragment (containing most of the hGH cDNA) via two oligonucleotides, HGH7 and HGH8:

```
                                    (SEQ ID NO: 5)
HGH7:      5'-TTAGGCTTATTCCCAAC-3'

(SEQ ID NO: 6)
HGH8:      5'-AATTGTTGGGAATAAGCC-3'
```

Figure 5:
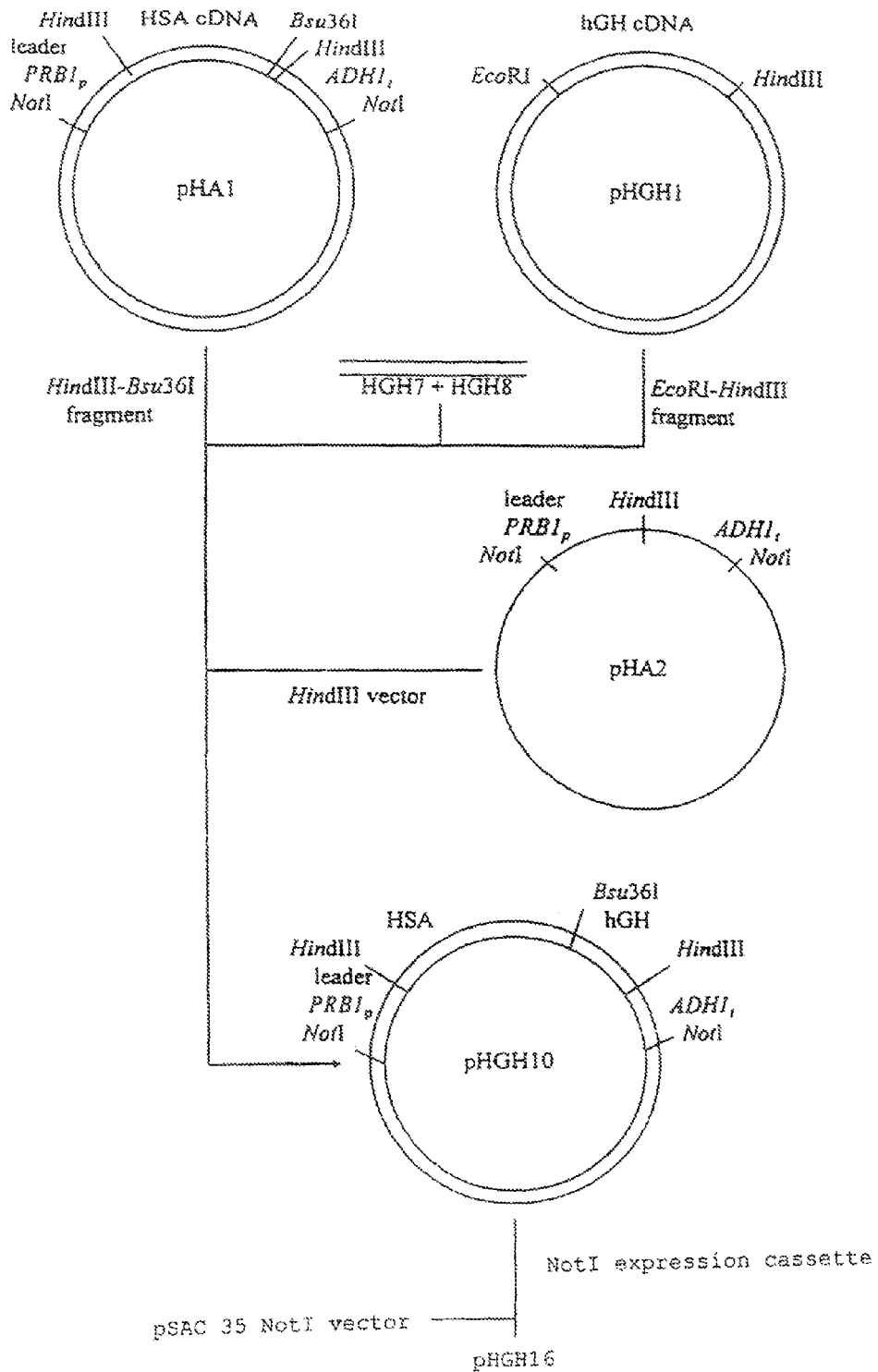
FIG. 5 shows the construction of pHGH16.

The HindIII fragment so formed was cloned into pHA2 digested with HindIII to make pHGH10 (FIG. 5), and the NotI expression cassette of this plasmid was cloned into NotI-digested pSAC35 to make pHGH16 (FIG. 5).

pHGH16 was used to transform S. cerevisiae DB1 and supernatants of cultures were analysed as in Example 2. A predominant band was observed that had a molecular weight of approximately 88 kD, corresponding to the combined masses of HA and hGH. Western blotting using anti-HSA and anti-hGH antisera (Sigma) confirmed the presence of the two constituent parts of the fusion protein.

The fusion protein was purified from culture supernatant by cation exchange chromatography, followed by anion exchange and gel permeation chromatography. Analysis of the N-terminus of the protein by amino acid sequencing confirmed the presence of the expected albumin sequence.

An in vitro growth hormone activity assay (Ealey et al, 1995) indicated that the fusion protein possessed full hGH activity, but that the potency was reduced compared to the hGH standard. In a hypophysectomised rat weight gain model, performed essentially as described in the European Pharmacopoeia (1987, monograph 556), the fusion molecule was more potent than hGH when the same number of units of activity (based on the above in vitro assay) were administered daily. Further experiments in which the fusion protein was administered once every four days showed a similar overall growth response to a daily administration of hGH. Pharmacokinetic experiments in which $^{125}$I-labelled protein was administered to rats indicated an approximately ten-fold increase in circulatory half life for the fusion protein compared to hGH (FIG. 12).

A similar plasmid was constructed in which DNA encoding the S.cerevisiae invertase (SUC2) leader sequence replaced the sequence for the hybrid leader, such that the encoded leader and the junction with the HSA sequence were as follows

```
        (showing amino acids 1-24 of SEQ ID NO: 7):
        MLLQAFLFLLAGFAAKISA↓DAHKS . . .
           Invertase leader   HSA
```

On introduction into S. cerevisiae DB1, this plasmid directed the expression and secretion of the fusion protein at a level similar to that obtained with pHGH16. Analysis of the N-terminus of the fusion protein indicated precise and efficient cleavage of the leader sequence from the mature protein.

EXAMPLE 4

Cloning and Expression of an hGH-HSA Fusion Protein

In order to fuse the hGH cDNA to the 5' end of the HSA cDNA (FIG. 6), the HSA cDNA was first altered by site-directed mutagenesis to introduce an EcoNI site near the 5' end of the coding region. This was done by the method of Kunkel et al (1987) using single-stranded DNA template prepared from pHA1 and a synthetic oligonucleotide, LEU4:

```
                                    (SEQ ID NO: 8)
LEU4:      5'-GAGATGCACACCTGAGTGAGG-3'
```

Site-directed mutagenesis using this oligonucleotide changed the coding sequence of the HSA cDNA from Lys4 to Leu4 (K4L). However, this change was repaired when the hGH cDNA was subsequently joined at the 5' end by linking the pHGH2 NotI-BamHI fragment to the EcoNI-NotI fragment of the mutated pHA1, via the two oligonucleotides HGH5 and HGH6:

```
                                              (SEQ ID NO: 9)
    HGH5:    5'-GATCCTGTGGCTTCGATGCACACAAGA-3'

(SEQ ID NO: 10)
    HGH6:    5'-CTCTTGTGTGCATCGAAGCCACAG-3'
```

The NotI fragment so formed was cloned into NotI-digested pSAC35 to make pHGH14 (FIG. 7). pHGH14 was used to transform *S. cerevisiae* DB1 and supernatants of cultures were analysed as in Example 2. A predominant band was observed that had a molecular weight of approximately 88 kD, corresponding to the combined masses of hGH and HA. Western blotting using anti-HSA and anti-hGH antisera confirmed the presence of the two constituent parts of the fusion protein.

The fusion protein was purified from culture supernatant by cation exchange chromatography, followed by anion exchange and gel permeation chromatography. Analysis of the N-terminus of the protein by amino acid sequencing confirmed the presence of the expected hGH sequence.

In vitro studies showed that the fusion protein retained hGH activity, but was significantly less potent than a fusion protein comprising full-length HA (1-585) as the N-terminal portion and hGH as the C-terminal portion, as described in Example 3.

EXAMPLE 5

Construction of Plasmids for the Expression of hGH Fusions to Domains of HSA Fusion polypeptides were made in which the hGH molecule was fused to the first two domains of HA (residues 1 to 387). Fusion to the N-terminus of hGH was achieved by joining the pHA1 HindIII-SapI fragment, which contained most of the coding sequence for domains 1 and 2 of HA, to the pHGH1 EcoRI-HindIII fragment, via the oligonucleotides HGH11 and HGH12:

```
                                              (SEQ ID NO: 11)
    HGH11:   5'-TGTGGAAGAGCCTCAGAATTTATTCCCAAC-3'

(SEQ ID NO: 12)
    HGH12:   5'-AATTGTTGGGAATAAATTCTGAGGCTCTTCC-3'
```

The HindIII fragment so formed was cloned into HindIII-digested pHA2 to make pHGH37 (FIG. 8) and the NotI expression cassette of this plasmid was cloned into NotI-digested pSAC35. The resulting plasmid, pHGH38 (FIG. 8), contained an expression cassette that was found to direct secretion of the fusion polypeptide into the supernatant when transformed into *S. cerevisiae* DB1. Western blotting using anti-HSA and anti-hGH antisera confirmed the presence of the two constituent parts of the fusion protein.

The fusion protein was purified from culture supernatant by cation exchange chromatography followed by gel permeation chromatography. In vivo studies with purified protein indicated that the circulatory half-life was longer than that of hGH, and similar to that of a fusion protein comprising full-length HA (1-585) as the N-terminal portion and hGH as the C-terminal portion, as described in Example 3. In vitro studies showed that the fusion protein retained hGH activity.

Using a similar strategy as detailed above, a fusion protein comprising the first domain of HA (residues 1-194) as the N-terminal portion and hGH as the C-terminal portion, was cloned and expressed in *S. cerevisiae* DB1. Western blotting of culture supernatant using anti-HSA and anti-hGH antisera confirmed the presence of the two constituent parts of the fusion protein.

EXAMPLE 6

Expression of hGH by Introducing a Cleavage Site Between HSA and hGH

Introduction of a peptide sequence that is recognised by the Kex2 protease, between the HA-hGH fusion protein, allows secretion of hGH. A sequence encoding Ser Leu Asp Lys Arg (SEQ ID NO: 13) was introduced using two oligonucleotides, HGH14 and HGH15:

```
                                              (SEQ ID NO: 14)
    HGH14:   5'-TTAGGCTTAAGCTTGGATAAAAGATTCCCAAC-3'

(SEQ ID NO: 15)
    HGH15:   5'-AATTGTTGGGAATCTTTTATCCAAGCTTAAGCC-3'
```

These were used to join the pHA1 HindIII-Bsu36I fragment to the pHGH1 EcoRI-HindIII fragment, which were then cloned into HindIII-digested pHA2 to make pHGH25 (FIG. 9). The NotI expression cassette of this plasmid was cloned into NotI-digested pSAC35 to make pHGH31 (FIG. 9).

*S. cerevisiae* DB1 transformed with pHGH31 was found to secrete two major species, as determined by SDS-PAGE analysis of culture supernatants. The two species had molecular weights of approximately 66 kD, corresponding to (full length) HA, and 22 kD, corresponding to (full length) hGH, indicating in vivo cleavage of the fusion protein by the Kex2 protease, or an equivalent activity. Western blotting using anti-HSA and anti-hGH antisera confirmed the presence of the two separate species. N-terminal sequence analysis of the hGH moiety confirmed the precise and efficient cleavage from the HA moiety.

The hGH moiety was purified from culture supernatant by anion exchange chromatography followed by gel permeation chromatography. In vitro studies with the purified hGH showed that the protein was active and fully potent.

Using a similar strategy, fusion proteins comprising either the first domain of HA (residues 1-194) or the first two domains of HA (residues 1-387), followed by a sequence recognised by the Kex2p protease, followed by the hGH cDNA, were cloned and expressed in *S. cerevisiae* DB1. Western blotting of culture supernatant using anti-HSA and anti-hGH antisera confirmed the presence of the two separate species.

EXAMPLE 7

Fusion of HSA to hGH Using a Flexible Linker Sequence

Flexible linkers, comprising repeating units of [Gly-Gly-Gly-Gly-Ser]$_n$, where n was either 2 (SEQ ID NO: 16) or 3 (SEQ ID NO: 17), were introduced between the HSA and hGH fusion protein by cloning of the oligonucleotides HGH16, HGH17, HGH18 and HGH19:

```
                                              (SEQ ID NO: 18)
HGH16:
5'-TTAGGCTTAGGTGGCGGTGGATCCGGCGGTGGTGGATCTTTCCCAA
C-3'

(SEQ ID NO: 19)
HGH17:
5'-AATTGTTGGGAAAGATCCACCACCGCCGGATCCACCGCCACCTAAGC
C-3'
```

-continued

HGH18: (SEQ ID NO: 20)
5'-TTAGGCTTAGGCGGTGGTGGATCTGGTGGCGGCGGATCTGGTGGCGG
TGGATCCTTCCCAAC-3'

HGH19: (SEQ ID NO: 21)
5'-AATTGTTGGGAAGGATCCACCGCCACCAGATCCGCCGCCACCAGATC
CACCACCGCCTAAGCC-3'

Annealing of HGH16 with HGH17 resulted in n=2, while HGH18 annealed to HGH19 resulted in n=3. After annealing, the double-stranded oligonucleotides were cloned with the EcoRI-Bsu36I fragment isolated from pHGH1 into Bsu36I-digested pHGH10 to make pHGH56 (where n=2) and pHGH57 (where n=3) (FIG. 10). The NotI expression cassettes from these plasmids were cloned into NotI-digested pSAC35 to make pHGH58 and pHGH59, respectively.

Cloning of the oligonucleotides to make pHGH56 and pHGH57 introduced a BamHI site in the linker sequences, as shown in FIG. 11. It was therefore possible to construct linker sequences in which n=1 and n=4, by joining either the HindIII-BamHI fragment from pHGH56 to the BamHI-HindIII fragment from pHGH57 (making n=1), or the HindIII-BamHI fragment from pHGH57 to the BamHI-HindIII fragment from pHGH56 (making n=2). Cloning of these fragments into the HindIII site of pHA2 (described in Example 2), resulted in pHGH60 (n=1) and pHGH61 (n=4) (see FIG. 11). The NotI expression cassettes from pHGH60 and pHGH61 were cloned into NotI-digested pSAC35 to make pHGH62 and pHGH63, respectively.

Transformation of S. cerevisiae with pHGH58, pHGH59, pHGH62 and pHGH63 resulted in transformants that secreted the fusion polypeptides into the supernatant.

Western blotting using anti-HSA and anti-hGH antisera confirmed the presence of the two constituent parts of the fusion proteins.

The fusion proteins were purified from culture supernatant by cation exchange chromatography, followed by anion exchange and gel permeation chromatography. Analysis of the N-termini of the proteins by amino acid sequencing confirmed the presence of the expected albumin sequence. Analysis of the purified proteins by electrospray mass spectrometry confirmed an increase in mass of 315 D (n=1), 630 D (n=2), 945 D (n=3) and 1260 D (n=4) compared to the HSA-hGH fusion protein described in Example 3, as expected. The purified protein was found to be active in vitro.

REFERENCES

Cunningham, B. C. et al (1991) Science 254, 821-825.
de Vos, A. M. et al (1992) Science 255, 306-312.
Ealey et al (1995) Growth Regulation 5, 36-44.
Gleeson et al (1986) J. Gen. Microbiol. 132, 3459-3465.
Haffner, D. et al, (1994) J. Clin. Invest. 93, 1163-1171.
Hiramitsu et al (1990) App. Env. Microbiol. 56, 2125-2132.
Hiramitsu et al (1991) ibid 57, 2052-2056.
Hoffman and Winston (1990) Genetics 124, 807-816.
Kearns, G. L. et al (1991) J. Clin. Endocrinol. Metab. 72, 1148-1156.
Kunkel, T. A. et al (1987) Methods in Enzymol. 154, 367-382.
Martial, J. A. et al (1979) Science 205, 602-607.
Maundrell (1990) J. Biol. Chem. 265, 10857-10864.
Nomura, N. et al (1995) Biosci. Biotech. Biochem. 59, 532-534.
Poznansky, M. J. et al (1988) FEBS Lett. 239, 18-22.
Saiki et al (1988) Science 239, 487-491.
Sambrook, J. et al (1989) Molecular Cloning: a Laboratory Manual, 2nd edition. Cold Spring Harbor Laboratory Press, Cold Spring Harbor, N.Y.
Sleep, D. et al (1990) Bio/Technology 8, 42-46.
Strobl, J. S. and Thomas, M. J. (1994) Pharmacol. Rev. 46, 1-34.
Tokunaga, T. et al (1985) Gene 39, 117-120.
Tsiomenko, A. B. et al (1994) Biochemistry (Moscow) 59, 1247-1256.
Zeisel, H. J. et al (1992) Horm. Res. 37 (Suppl. 2), 5-13.

The invention claimed is:

1. An isolated polypeptide consisting of a continuous region of amino acids joined together by peptide bonds and comprising a first region, which is a variant or fragment of mature growth hormone (GH) and has at least 90% sequence identity with a same-length region of GH, and a second region, which is a variant or fragment of mature serum albumin and has at least 75% sequence identity with a same-length region of serum albumin, wherein (i) said isolated polypeptide has a higher circulatory half-life than a polypeptide comprising the first region but not the second region, and (ii) said isolated polypeptide binds and activates the GH receptor.

2. An isolated polypeptide according to claim 1 in which each of said first and second regions has at least 95% sequence identity with the said lengths of GH and albumin, respectively.

3. An isolated polypeptide according to claim 2 wherein each of said first and second regions is at least 50 amino acids long.

4. An isolated polypeptide according to claim 1 wherein the first region consists of uninterrupted amino acids of the C-terminus of GH, or a conservative modification thereof.

5. An isolated polypeptide according to claim 4 wherein the first region is 191 amino acids long.

6. An isolated polypeptide according to claim 1 wherein the albumin and/or the growth hormone is human.

7. An isolated polypeptide according to claim 1 wherein the second region comprises at least one uninterrupted domain of albumin or a conservative modification thereof.

8. An isolated polypeptide according to claim 7 wherein the second region comprises uninterrupted amino acids 1-105, 120-194, 195-291, 316-387, 388-491, 512-585, 1-194, 195-387, 388-585, 1-387or 195-585 of human albumin or a conservative modification thereof.

9. An isolated polypeptide according to claim 1 wherein the N-terminus of the polypeptide comprises the said first region and the C-terminus comprises the said second region.

10. An isolated polypeptide according to claim 1 wherein the N-terminus of the polypeptide comprises the said second region and the C-terminus comprises the said first region.

11. An isolated polypeptide according to claim 1 which consists of the said first and second regions, optionally with further amino acids or other compounds added to either end of the polypeptide.

12. A microbial culture medium comprising transformed cells and a polypeptide according to claim 1.

13. A microbial culture medium comprising a polypeptide according to claim 1.

14. A polynucleotide encoding a polypeptide according to claim 1.

15. A microbial host comprising a polynucleotide according to claim 14 arranged for expression in the host.

16. A host according to claim 15 wherein the polypeptide is secreted from the host.

17. A pharmaceutical formulation comprising a polypeptide according to claim 1 and a pharmaceutically acceptable carrier.

* * * * *

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 1:

CCCAAGAATT CCCTTATCCA GGC 23

(2) INFORMATION FOR SEQ ID NO: 2:

(i) SEQUENCE CHARACTERISTICS:
      (A) LENGTH: 33 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 2:

GGGAAGCTTA GAAGCCACAG GATCCCTCCA CAG    33

(2) INFORMATION FOR SEQ ID NO: 3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE LINKER"

(iii) HYPOTHETICAL: NO (iv) ANTI-SENSE: No (xi) SEQUENCE DESCRIPTION: SEQ ID NO: 3:

GATAAAGATT CCCAAC    16

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 4:

AATTGTTGGG AATCTTT    17

(2) INFORMATION FOR SEQ ID NO: 5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 5:

TTAGGCTTAT TCCCAAC    17

(2) INFORMATION FOR SEQ ID NO: 6:

(i) SEQUENCE CHARACTERISTICS:
        (A) LENGTH: 18 base pairs

-continued (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 6:

AATTGTTGGG AATAAGCC    18

(2) INFORMATION FOR SEQ ID NO: 7:

(i) SEQUENCE CHARACTERISTICS:
        (A) LENGTH: 604 amino acids
        (B) TYPE: amino acid
        (C) STRANDEDNESS: <Unknown>
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 7:

```
Met Leu Leu Gln Ala Phe Leu Phe Leu Leu Ala Gly Phe Ala Ala Lys
 1               5                  10                  15

Ile Ser Ala Asp Ala His Lys Ser Glu Val Ala His Arg Phe Lys Asp
            20                  25                  30

Leu Gly Glu Glu Asn Phe Lys Ala Leu Val Leu Ile Ala Phe Ala Gln
        35                  40                  45

Tyr Leu Gln Gln Cys Pro Phe Glu Asp His Val Lys Leu Val Asn Glu
50                  55                  60

Val Thr Glu Phe Ala Lys Thr Cys Val Ala Asp Glu Ser Ala Glu Asn
65                  70                  75                  80

Cys Asp Lys Ser Leu His Thr Leu Phe Gly Asp Lys Leu Cys Thr Val
                85                  90                  95

Ala Thr Leu Arg Glu Thr Tyr Gly Glu Met Ala Asp Cys Cys Ala Lys
            100                 105                 110

Gln Glu Pro Glu Arg Asn Glu Cys Phe Leu Gln His Lys Asp Asp Asn
        115                 120                 125

Pro Asn Leu Pro Arg Leu Val Arg Pro Glu Val Asp Val Met Cys Thr
130                 135                 140

Ala Phe His Asp Asn Glu Glu Thr Phe Leu Lys Lys Tyr Leu Tyr Glu
145                 150                 155                 160

Ile Ala Arg Arg His Pro Tyr Phe Tyr Ala Pro Glu Leu Leu Phe Phe
                165                 170                 175

Ala Lys Arg Tyr Lys Ala Ala Phe Thr Glu Cys Cys Gln Ala Ala Asp
            180                 185                 190

Lys Ala Ala Cys Leu Leu Pro Lys Leu Asp Glu Leu Arg Asp Glu Gly
        195                 200                 205

Lys Ala Ser Ser Ala Lys Gln Arg Leu Lys Cys Ala Ser Leu Gln Lys
210                 215                 220

Phe Gly Glu Arg Ala Phe Lys Ala Trp Ala Val Ala Arg Leu Ser Gln
225                 230                 235                 240

Arg Phe Pro Lys Ala Glu Phe Ala Glu Val Ser Lys Leu Val Thr Asp
                245                 250                 255
```

```
      Leu Thr Lys Val His Thr Glu Cys Cys His Gly Asp Leu Leu Glu Cys
                  260                 265                 270

Ala Asp Asp Arg Ala Asp Leu Ala Lys Tyr Ile Cys Glu Asn Gln Asp
                  275                 280                 285

Ser Ile Ser Ser Lys Leu Lys Glu Cys Cys Glu Lys Pro Leu Leu Glu
                  290                 295                 300

Lys Ser His Cys Ile Ala Glu Val Glu Asn Asp Glu Met Pro Ala Asp
      305                 310                 315                 320

Leu Pro Ser Leu Ala Ala Asp Phe Val Glu Ser Lys Asp Val Cys Lys
                  325                 330                 335

Asn Tyr Ala Glu Ala Lys Asp Val Phe Leu Gly Met Phe Leu Tyr Glu
                  340                 345                 350

Tyr Ala Arg Arg His Pro Asp Tyr Ser Val Val Leu Leu Leu Arg Leu
                  355                 360                 365

Ala Lys Thr Tyr Glu Thr Thr Leu Glu Lys Cys Cys Ala Ala Ala Asp
                  370                 375                 380

Pro His Glu Cys Tyr Ala Lys Val Phe Asp Glu Phe Lys Pro Leu Val
      385                 390                 395                 400

Glu Glu Pro Gln Asn Leu Ile Lys Gln Asn Cys Glu Leu Phe Glu Gln
                  405                 410                 415

Leu Gly Glu Tyr Lys Phe Gln Asn Ala Leu Leu Val Arg Tyr Thr Lys
                  420                 425                 430

Lys Val Pro Gln Val Ser Thr Pro Thr Leu Val Glu Val Ser Arg Asn
                  435                 440                 445

Leu Gly Lys Val Gly Ser Lys Cys Cys Lys His Pro Glu Ala Lys Arg
                  450                 455                 460

Met Pro Cys Ala Glu Asp Tyr Leu Ser Val Val Leu Asn Gln Leu Cys
      465                 470                 475                 480

Val Leu His Glu Lys Thr Pro Val Ser Asp Arg Val Thr Lys Cys Cys
                  485                 490                 495

Thr Glu Ser Leu Val Asn Arg Arg Pro Cys Phe Ser Ala Leu Glu Val
                  500                 505                 510

Asp Glu Thr Tyr Val Pro Lys Glu Phe Asn Ala Glu Thr Phe Thr Phe
                  515                 520                 525

His Ala Asp Ile Cys Thr Leu Ser Glu Lys Glu Arg Gln Ile Lys Lys
                  530                 535                 540

Gln Thr Ala Leu Val Glu Leu Val Lys His Lys Pro Lys Ala Thr Lys
      545                 550                 555                 560

Glu Gln Leu Lys Ala Val Met Asp Asp Phe Ala Ala Phe Val Glu Lys
                  565                 570                 575

Cys Cys Lys Ala Asp Asp Lys Glu Thr Cys Phe Ala Glu Glu Gly Lys
                  580                 585                 590

Lys Leu Val Ala Ala Ser Gln Ala Ala Leu Gly Leu
                  595                 600

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE FOR USE IN (iii) HYPOTHETICAL: NO
```

```
       (iv) ANTI-SENSE: NO (xi) SEQUENCE DESCRIPTION: SEQ ID NO: 8:

GAGATGCACA CCTGAGTGAG G                                           21

(2) INFORMATION FOR SEQ ID NO: 9:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 9:

GATCCTGTGG CTTCGATGCA CACAAGA                                    27

(2) INFORMATION FOR SEQ ID NO: 10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 10:

CTCTTGTGTG CATCGAAGCC ACAG                                       24

(2) INFORMATION FOR SEQ ID NO: 11:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 11:

TGTGGAAGAG CCTCAGAATT TATTCCCAAC                                 30

(2) INFORMATION FOR SEQ ID NO: 12:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE LINKER"

(iii) HYPOTHETICAL: NO
```

(iv) ANTI-SENSE: NO (xi) SEQUENCE DESCRIPTION: SEQ ID NO: 12:

AATTGTTGGG AATAAATTCT GAGGCTCTTC C        31

(2) INFORMATION FOR SEQ ID NO: 13:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 13:

Ser Leu Asp Lys Arg
        1               5

(2) INFORMATION FOR SEQ ID NO: 14:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE LINKER"

(iii) HYPOTHETICAL: NO (iv) ANTI-SENSE: NO (xi) SEQUENCE DESCRIPTION: SEQ ID NO: 14:

TTAGGCTTAA GCTTGGATAA AAGATTCCCA AC        32

(2) INFORMATION FOR SEQ ID NO: 15:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA OLIGONUCLEOTIDE"

(iii) HYPOTHETICAL: NO (iv) ANTI-SENSE: NO (xi) SEQUENCE DESCRIPTION: SEQ ID NO: 15:

AATTGTTGGG AATCTTTTAT CCAAGCTTAA GCC        33

(2) INFORMATION FOR SEQ ID NO: 16:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 16:

Gly Gly Gly Gly Ser Gly Gly Gly Gly Ser
1               5                   10

(2) INFORMATION FOR SEQ ID NO: 17:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 17:

Gly Gly Gly Gly Ser Gly Gly Gly Gly Ser Gly Gly Gly Gly Ser
1               5                   10                  15

(2) INFORMATION FOR SEQ ID NO: 18:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE ENCODING (iii) HYPOTHETICAL: NO (iv) ANTI-SENSE: NO (xi) SEQUENCE DESCRIPTION: SEQ ID NO: 18:

TTAGGCTTAG GTGGCGGTGG ATCCGGCGGT GGTGGATCTT TCCCAAC      47

(2) INFORMATION FOR SEQ ID NO: 19:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE ENCODING (iii) HYPOTHETICAL: NO (iv) ANTI-SENSE: NO (xi) SEQUENCE DESCRIPTION: SEQ ID NO: 19:

AATTGTTGGG AAAGATCCAC CACCGCCGGA TCCACCGCCA CCTAAGCC     48

(2) INFORMATION FOR SEQ ID NO: 20:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE ENCODING (iii) HYPOTHETICAL: NO

```
        (iv) ANTI-SENSE: NO (xi) SEQUENCE DESCRIPTION: SEQ ID NO: 20:

TTAGGCTTAG GCGGTGGTGG ATCTGGTGGC GGCGGATCTG GTGGCGGTGG ATCCTTCCCA      60

AC                                                                62

(2) INFORMATION FOR SEQ ID NO: 21:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGONUCLEOTIDE ENCODING (iii) HYPOTHETICAL: NO (iv) ANTI-SENSE: NO (xi) SEQUENCE DESCRIPTION: SEQ ID NO: 21:

AATTGTTGGG AAGGATCCAC CGCCACCAGA TCCGCCGCCA CCAGATCCAC CACCGCCTAA      60

GCC                                                               63

(2) INFORMATION FOR SEQ ID NO: 22:

(i) SEQUENCE CHARACTERISTICS:
            (A) LENGTH: 576 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 22:

TTCCCAACCA TTCCCTTATC CAGGCTTTTT GACAACGCTA TGCTCCGCGC CCATCGTCTG      60

CACCAGCTGG CCTTTGACAC CTACCAGGAG TTTGAAGAAG CCTATATCCC AAAGGAACAG     120

AAGTATTCAT TCCTGCAGAA CCCCCAGACC TCCCTCTGTT TCTCAGAGTC TATTCCGACA     180

CCCTCCAACA GGGAGGAAAC ACAACAGAAA TCCAACCTAG AGCTGCTCCG CATCTCCCTG     240

CTGCTCATCC AGTCGTGGCT GGAGCCCGTG CAGTTCCTCA GGAGTGTCTT CGCCAACAGC     300

CTGGTGTACG GCGCCTCTGA CAGCAACGTC TATGACCTCC TAAAGGACCT AGAGGAAGGC     360

ATCCAAACGC TGATGGGGAG GCTGGAAGAT GGCAGCCCCC GGACTGGGCA GATCTTCAAG     420

CAGACCTACA GCAAGTTCGA CACAAACTCA CACAACGATG ACGCACTACT CAAGAACTAC     480

GGGCTGCTCT ACTGCTTCAG GAAGGACATG GACAAGGTCG AGACATTCCT GCGCATCGTG     540

CAGTGCCGCT CTGTGGAGGG CAGCTGTGGC TTCTAG                              576

(2) INFORMATION FOR SEQ ID NO: 23:

(i) SEQUENCE CHARACTERISTICS:
            (A) LENGTH: 191 amino acids
            (B) TYPE: amino acid
            (C) STRANDEDNESS: <Unknown>
            (D) TOPOLOGY: linear (ii) MOLECULE TYPE: protein (iii) HYPOTHETICAL: NO
```

(iv) ANTI-SENSE: NO (xi) SEQUENCE DESCRIPTION: SEQ ID NO: 23:

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
             35                  40                  45

Gln Thr Ser Leu Cys Phe Ser Glu Ser Ile Pro Thr Pro Ser Asn Arg
         50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
             115                 120                 125

Glu Asp Gly Ser Pro Arg Thr Gly Gln Ile Phe Lys Gln Thr Tyr Ser
         130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190
```

(2) INFORMATION FOR SEQ ID NO: 24:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide linker"

(iii) HYPOTHETICAL: NO (iv) ANTI-SENSE: NO (xi) SEQUENCE DESCRIPTION: SEQ ID NO: 24:

```
AAGCTCCTAG GCCCGGGCGG CCGCAAGCTT GTCGACGCTA GCTGCAGAAG GATCCAGATC    60

TCGAGGCGCC ATCGATAATT C                                              81
```

(2) INFORMATION FOR SEQ ID NO: 25:

(i) SEQUENCE CHARACTERISTICS:
        (A) LENGTH: 1758 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 25:

```
GATGCACACA AGAGTGAGGT TGCTCATCGG TTTAAAGATT TGGGAGAAGA AAATTTCAAA    60
```

-continued

```
GCCTTGGTGT TGATTGCCTT TGCTCAGTAT CTTCAGCAGT GTCCATTTGA AGATCATGTA      120

AAATTAGTGA ATGAAGTAAC TGAATTTGCA AAAACATGTG TTGCTGATGA GTCAGCTGAA      180

AATTGTGACA ATCACTTCA TACCCTTTTT GGAGACAAAT TATGCACAGT TGCAACTCTT      240

CGTGAAACCT ATGGTGAAAT GGCTGACTGC TGTGCAAAAC AAGAACCTGA GAGAAATGAA      300

TGCTTCTTGC AACACAAAGA TGACAACCCA AACCTCCCCC GATTGGTGAG ACCAGAGGTT      360

GATGTGATGT GCACTGCTTT TCATGACAAT GAAGAGACAT TTTTGAAAAA ATACTTATAT      420

GAAATTGCCA AAGACATCC TTACTTTTAT GCCCCGGAAC TCCTTTTCTT TGCTAAAAGG       480

TATAAAGCTG CTTTTACAGA ATGTTGCCAA GCTGCTGATA AAGCTGCCTG CCTGTTGCCA      540

AAGCTCGATG AACTTCGGGA TGAAGGGAAG CTTCGTCTG CCAAACAGAG ACTCAAGTGT       600

GCCAGTCTCC AAAAATTTGG AGAAAGAGCT TTCAAAGCAT GGGCAGTAGC TCGCCTGAGC      660

CAGAGATTTC CCAAAGCTGA GTTTGCAGAA GTTTCCAAGT TAGTGACAGA TCTTACCAAA      720

GTCCACACGG AATGCTGCCA TGGAGATCTG CTTGAATGTG CTGATGACAG GCGGACCTT       780

GCCAAGTATA TCTGTGAAAA TCAAGATTCG ATCTCCAGTA AACTGAAGGA ATGCTGTGAA      840

AAACCTCTGT TGGAAAAATC CCACTGCATT GCCGAAGTGG AAAATGATGA ATGCCTGCT       900

GACTTGCCTT CATTAGCTGC TGATTTTGTT GAAAGTAAGG ATGTTTGCAA AACTATGCT       960

GAGGCAAAGG ATGTCTTCCT GGGCATGTTT TTGTATGAAT ATGCAAGAAG GCATCCTGAT     1020

TACTCTGTCG TGCTGCTGCT GAGACTTGCC AAGACATATG AAACCACTCT AGAGAAGTGC     1080

TGTGCCGCTG CAGATCCTCA TGAATGCTAT GCCAAAGTGT TCGATGAATT TAAACCTCTT     1140

GTGGAAGAGC CTCAGAATTT AATCAAACAA AATTGTGAGC TTTTTGAGCA GCTTGGAGAG     1200

TACAAATTCC AGAATGCGCT ATTAGTTCGT TACACCAAGA AAGTACCCCA AGTGTCAACT     1260

CCAACTCTTG TAGAGGTCTC AAGAAACCTA GGAAAAGTGG GCAGCAAATG TTGTAAACAT     1320

CCTGAAGCAA AAAGAATGCC CTGTGCAGAA GACTATCTAT CCGTGGTCCT GAACCAGTTA     1380

TGTGTGTTGC ATGAGAAAAC GCCAGTAAGT GACAGAGTCA CCAAATGCTG CACAGAATCC     1440

TTGGTGAACA GGCGACCATG CTTTTCAGCT CTGGAAGTCG ATGAAACATA CGTTCCCAAA     1500

GAGTTTAATG CTGAAACATT CACCTTCCAT GCAGATATAT GCACACTTTC TGAGAAGGAG     1560

AGACAAATCA AGAAACAAAC TGCACTTGTT GAGCTCGTGA ACACAAGCC CAAGGCAACA      1620

AAAGAGCAAC TGAAAGCTGT TATGGATGAT TTCGCAGCTT TTGTAGAGAA GTGCTGCAAG     1680

GCTGACGATA AGGAGACCTG CTTTGCCGAG GAGGGTAAAA AACTTGTTGC TGCAAGTCAA     1740

GCTGCCTTAG GCTTATAA                                                    1758
```

(2) INFORMATION FOR SEQ ID NO: 26:

(i) SEQUENCE CHARACTERISTICS:
      (A) LENGTH: 585 amino acids
      (B) TYPE: amino acid
      (C) STRANDEDNESS: <Unknown>
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 26:

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
```

```
                      20                  25                  30
        Gln Cys Pro Phe Glu Asp His Val Lys Leu Val Asn Glu Val Thr Glu
                    35                  40                  45

Phe Ala Lys Thr Cys Val Ala Asp Glu Ser Ala Glu Asn Cys Asp Lys
                    50                  55                  60

Ser Leu His Thr Leu Phe Gly Asp Lys Leu Cys Thr Val Ala Thr Leu
        65                  70                  75                  80

Arg Glu Thr Tyr Gly Glu Met Ala Asp Cys Cys Ala Lys Gln Glu Pro
                        85                  90                  95

Glu Arg Asn Glu Cys Phe Leu Gln His Lys Asp Asp Asn Pro Asn Leu
                    100                 105                 110

Pro Arg Leu Val Arg Pro Glu Val Asp Val Met Cys Thr Ala Phe His
                    115                 120                 125

Asp Asn Glu Glu Thr Phe Leu Lys Lys Tyr Leu Tyr Glu Ile Ala Arg
                    130                 135                 140

Arg His Pro Tyr Phe Tyr Ala Pro Glu Leu Leu Phe Phe Ala Lys Arg
        145                 150                 155                 160

Tyr Lys Ala Ala Phe Thr Glu Cys Cys Gln Ala Ala Asp Lys Ala Ala
                        165                 170                 175

Cys Leu Leu Pro Lys Leu Asp Glu Leu Arg Asp Glu Gly Lys Ala Ser
                    180                 185                 190

Ser Ala Lys Gln Arg Leu Lys Cys Ala Ser Leu Gln Lys Phe Gly Glu
                    195                 200                 205

Arg Ala Phe Lys Ala Trp Ala Val Ala Arg Leu Ser Gln Arg Phe Pro
                    210                 215                 220

Lys Ala Glu Phe Ala Glu Val Ser Lys Leu Val Thr Asp Leu Thr Lys
        225                 230                 235                 240

Val His Thr Glu Cys Cys His Gly Asp Leu Leu Glu Cys Ala Asp Asp
                        245                 250                 255

Arg Ala Asp Leu Ala Lys Tyr Ile Cys Glu Asn Gln Asp Ser Ile Ser
                    260                 265                 270

Ser Lys Leu Lys Glu Cys Cys Glu Lys Pro Leu Leu Glu Lys Ser His
                    275                 280                 285

Cys Ile Ala Glu Val Glu Asn Asp Glu Met Pro Ala Asp Leu Pro Ser
                    290                 295                 300

Leu Ala Ala Asp Phe Val Glu Ser Lys Asp Val Cys Lys Asn Tyr Ala
        305                 310                 315                 320

Glu Ala Lys Asp Val Phe Leu Gly Met Phe Leu Tyr Glu Tyr Ala Arg
                        325                 330                 335

Arg His Pro Asp Tyr Ser Val Val Leu Leu Leu Arg Leu Ala Lys Thr
                    340                 345                 350

Tyr Glu Thr Thr Leu Glu Lys Cys Cys Ala Ala Ala Asp Pro His Glu
                    355                 360                 365

Cys Tyr Ala Lys Val Phe Asp Glu Phe Lys Pro Leu Val Glu Glu Pro
                    370                 375                 380

Gln Asn Leu Ile Lys Gln Asn Cys Glu Leu Phe Glu Gln Leu Gly Glu
        385                 390                 395                 400

Tyr Lys Phe Gln Asn Ala Leu Leu Val Arg Tyr Thr Lys Lys Val Pro
                        405                 410                 415

Gln Val Ser Thr Pro Thr Leu Val Glu Val Ser Arg Asn Leu Gly Lys
                    420                 425                 430

Val Gly Ser Lys Cys Cys Lys His Pro Glu Ala Lys Arg Met Pro Cys
                    435                 440                 445
```

```
Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
        515             520             525

Leu Val Glu Leu Val Lys His Lys Pro Lys Ala Thr Lys Glu Gln Leu
    530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585
```